US009539559B2

(12) United States Patent
Chen et al.

(10) Patent No.: US 9,539,559 B2
(45) Date of Patent: Jan. 10, 2017

(54) METAL-ORGANIC FRAMEWORKS FOR SELECTIVE SEPARATIONS

(71) Applicant: THE BOARD OF REGENTS OF THE UNIVERSITY OF TEXAS SYSTEM, Austin, TX (US)

(72) Inventors: Banglin Chen, San Antonio, TX (US); Chuande Wu, San Antonio, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 14/766,132

(22) PCT Filed: Feb. 5, 2014

(86) PCT No.: PCT/US2014/014901
§ 371 (c)(1),
(2) Date: Aug. 5, 2015

(87) PCT Pub. No.: WO2014/130246
PCT Pub. Date: Aug. 28, 2014

(65) Prior Publication Data
US 2015/0360201 A1    Dec. 17, 2015

Related U.S. Application Data

(60) Provisional application No. 61/761,592, filed on Feb. 6, 2013.

(51) Int. Cl.
*B01J 20/22*  (2006.01)
*B01D 53/04*  (2006.01)
(Continued)

(52) U.S. Cl.
CPC .............. *B01J 20/226* (2013.01); *B01D 53/04* (2013.01); *C01B 3/56* (2013.01); *C07F 1/08* (2013.01);
(Continued)

(58) Field of Classification Search
CPC ..... B01J 20/226; C01B 3/56; C01B 2203/042; C01B 2210/0051; C01B 2210/007; C07F 1/08; B01D 53/04; B01D 2253/204
(Continued)

(56) References Cited

U.S. PATENT DOCUMENTS 7,662,746 B2    2/2010 Yaghi et al.
2011/0046335 A1    2/2011 Fernandes
(Continued)

FOREIGN PATENT DOCUMENTS

WO    WO 2012/122233    9/2012

OTHER PUBLICATIONS

Allan et al., "Thermal, spectral and magnetic studies of some compounds of cobalt (II), nickel (II), and copper (II) with cinnamic acid", *Termochimica Acta*, 154: 315-322, 1989.
(Continued)

*Primary Examiner* — Frank Lawrence
(74) *Attorney, Agent, or Firm* — Parker Highlander PLLC

(57) ABSTRACT

Disclosed herein are metal-organic frameworks (MOF) and uses thereof, including those comprising a repeat unit of the formula [Cu3(L1)2(H2O)3] or [Cu3(L2)2(H2O)3], wherein L1 is a ligand of the formula: (structurally represented), and where L2 is a ligand of the formula: (structurally represented). These are useful for many applications, including in the purification of hydrogen gas from production byproducts CH4 and CO2, sensing, heterogeneous catalysis, drug delivery, lithium sulfide battery, membrane and analytical devices.

(Continued)

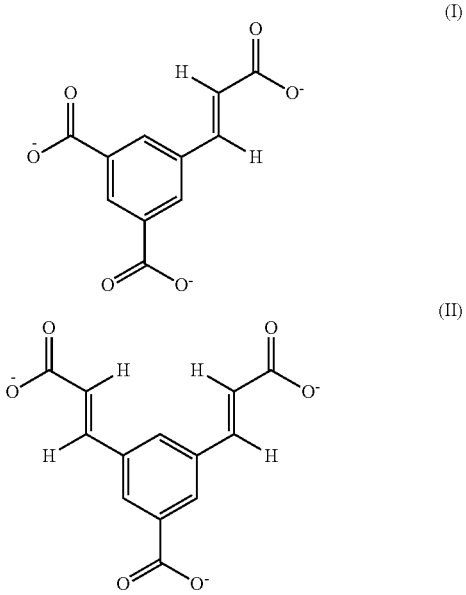

37 Claims, 10 Drawing Sheets

(51) Int. Cl.
C07F 1/08 (2006.01)
C01B 3/56 (2006.01)
(52) U.S. Cl.
CPC ... B01D 2253/204 (2013.01); C01B 2203/042 (2013.01); C01B 2210/007 (2013.01); C01B 2210/0051 (2013.01)
(58) Field of Classification Search
USPC ...... 95/90, 139, 143, 900, 902; 96/108, 154; 502/401
See application file for complete search history.

(56) References Cited

U.S. PATENT DOCUMENTS

| | | | |
|---|---|---|---|
| 2012/0028846 A1 | 2/2012 | Yaghi et al. | |
| 2012/0073438 A1 | 3/2012 | Ryan et al. | |
| 2013/0139686 A1* | 6/2013 | Wilmer | B01J 20/223 95/127 |
| 2015/0071845 A1* | 3/2015 | Zhou | B01J 20/226 423/437.1 |

OTHER PUBLICATIONS

Bae et al., "Separation of gas mixtures using Co(II) carborane-base porous coordination polymers", Chem. Commun., 46:3478-80, 2010.
Bloch et al., "Hydrocarbon separations in a metal-organic framework with open iron(II) coordination sites", Science 335:1606-1610, 2012.
Chen et al., "A microporous metal-organic framework for gas-chromatographic", Angew. Chem., Int. Ed., 45:1390-93, 2006.
Chen et al., "High $H_2$ adsorption in a microporous metal-organic framework with open metal sites", Angew. Chem., 117: 4823-4827, 2005.
Chen et al., "Metal-organic frameworks with functional pores for recognition of small molecules", Acc. Chem. Res., 43:1115-24, 2010.
Chen et al., "Porous Cu—Cd mixed-metal-organic frameworks constructed from Cu(Pyac)2 [Bis[3-(4-pyridyl)pentane-2,4-dionato]copper(II)]", Inorg. Chem., 43:8209-11, 2004.
Chen et al., "Surface interaction and quantum kinetic molecular sieving for H2 and D2 adsorption on a mixed metal-organic framework material", J. Am. Chem. Soc., 130:6411-23, 2008.
Chen, et al., "Interwoven metal-organic framework on a periodic minimal surface with extra-large pores", Science, 291:1021-3, 2001.
Cho et al., "A metal-organic framework material that functions as an enantioselective catalyst for olefin epoxidation", Chem. Commun., 24: 2563-5, 2006.
Chowdhury et al., "Adsorption of CO, $CO_2$ and $CH_4$ on Cu-BTC and MIL-101 metal organic frameworks: effect of open metal sites and adsorbate polarity", Microporous Mesoporous Mater., 152:246-252, 2012.
Deng et al., "Multiple functional groups of varying ratios in metal-organic frameworks", Science, 327:846, 2010.
Dubbeldam et al., "Separation and molecular-level segregation of complex alkane mixtures in metal-organic frameworks", J. Am. Chem. Soc., 130:10884-5, 2008.
Dybtsev et al., "A homochiral metal-organic material with permanent porosity, enantioselective sorption properties, and catalytic activity", Angew. Chem., Int. Ed., 45:916-20, 2006.
Dybtsev et al., "Microporous manganese formate: a simple metal-organic porous material with high framework stability and highly selective gas sorption properties", J. Am. Chem. Soc., 126:32, 2004.
Farha, et al., "De novo synthesis of a metal-organic framework material featuring ultrahigh surface area and gas storage capacities", Nature Chem., 2: 944-948, 2010.
Farha, et al., "Metal-organic framework materials with ultrahigh surface areas: is the sky the limit?", J. Am. Chem. Soc., 134:15016-21, 2012.
Finsy et al., "Pore-filling-dependent selectivity effects in the vapor-phase separation of xylene isomers on the metal-organic framework MIL-47", J. Am. Chem. Soc., 130:7110-7118, 2008.
Furukawa, et al., "Isoreticular expansion of metal-organic frameworks with triangular and square building units and the lowest calculated density for porous crystals", Inorg. Chem., 50:9147-52, 2011.
Furukawa, et al., "Ultrahigh porosity in metal-organic frameworks", Science, 329:424-428, 2010.
Gedrich, et al., "A highly porous metal-organic framework with open nickel sites",Angew. Chem.Int. Ed., 49:8489-8452, 2010.
Grünker, et al., "Dye encapsulation inside a new mesoporous metal-organic frameworks for multifunctional solvatochromic-response function", Chem. Eur.J., 18:13299-13303, 2012.
Guo, et al, "'Twin copper source' growth of metal—organic framework membrane: Cu(3) (BTC)(2) with high permeability and selectivity for recycling H(2)", J. Am. Chem. Soc., 131:1646-7, 2009.
Guo, et al, "A metal-organic framework with optimized open metal sites and pore spaces for high methane storage at room temperature", Angew. Chem. Int. Ed.., 50:3178-3181, 2011.
He, et al, "A microporous metal-organic framework for highly selective separation of acetylene, ethylene, and ethane from methane at room temperature", Chem. Eur. J., 18:613-619, 2012.
He, et al, "A robust doubly interpenetrated metal-organic framework constructed from a novel aromatic tricarboxylate for highly selective separation of small hydrocarbons", Chem. Commun., 48:6493-6495, 2012.
He, et al, "High separation capacity and selectivity of C2 hydrocarbons over methane within a microporous metal-organic framework at room temperature", Chem Eur. J., 18:1901-1904, 2012.
He, et al, "Metal-organic frameworks with potential for energy-efficient adsorptive separation of light hydrocarbons", Energy Environ. Sci. 5: 9107-9120, 2012.
He, et al., "A microporous metal-organic framework assembled from an aromatic tetracarboxylate for $H_2$ purification", J. Mater. Chem. A.., 1: 2543-2551, 2013.
Herm, et al., "Reprint of: $CO_2/CH_4$, $CH_4/H_2$ and $CO_2/CH_4/H_2$ separations at high pressures using $Mg_2$(dobdc)", Micropor. Mesopor. Mater., 157:94-100, 2012.

(56) References Cited

OTHER PUBLICATIONS

Herm, et al., "$CO_2/CH_4$, $CH_4/H_2$ and $CO_2/CH_4/H_2$ separations at high pressures using $Mg_2$(dobdc)", *Micropor. Mesopor. Mater.*, 151:481-487, 2012.
Herm, et al., "Metal-organic frameworks as adsorbents for hydrogen purification and precombustion carbon dioxide capture", *J. Am. Chem. Soc.*, 133:5664-5667, 2011.
Horike et al., "Soft porous crystals", *Nature Chem.*, 1:695, 2009.
Hu, et al., "A new MOF-505 analog exhibiting high acetylene storage", *Chem. Commun.*, 7551-3, 2009.
International Preliminary Report on Patentability issued in International Application No. PCT/US14/14901, mailed Aug. 11, 2015.
International Search Report and Written Opinion issued in International Application No. PCT/US14/14901, mailed Jun. 3, 2014.
Kaye, et al., "Impact of preparation and handling on the hydrogen storage properties of $Zn_4O(1,4-benzenedicarboxylate)_3$ (MOF-5)", *J. Am. Chem. Soc.*, 129:14176-14177, 2007.
Khan et al., "Facile syntheses of metal-organic framework $Cu_3(BTC)_2(H2O)_3$ under ultrasound", *Bull. Korean Chem. Soc.*, 30(12): 2921-2926, 2009. Abstract.
Kitaura et al., "Immobilization of a metallo Schiff base into a microporous coordination polymer", *Angew. Chem., Int. Ed.*, 43:2684, 2004.
Kong et al., "Expanded organic building units for the construction of highly porous metal-organic organic frameworks", *Chem. Eur. J.*, 19(44): 14886-14894, 2013.
Krishna and Baur, "Modelling issues in zeolite based separation processes", *Sep. Purif. Technol.*, 33:213-254, 2003.
Krishna and Long, "Screening metal-organic frameworks by analysis of transient breakthrough of gas mixtures in a fixed bed adsorber", *J. Phys. Chem. C.*, 115:12941-12950, 2011.
Krishna and van Baten, "A comparison of the $CO_2$ capture characteristics of zeolites an metal-organic frameworks", *Sep. Purif. Technol.* 8:120-126, 2012.
Krishna, "Adsorptive separation of $CO_2/CH_4/CO$ gas mixtures at high pressures", *Microporous, Mesoporous, Mater.*, 156: 217-223, 2012.
Latroche, et al., "Hydrogen storage in the giant-pore metal-organic frameworks MIL-100 and MIL-101", *Angew. Chem. Int. Ed.*, 45:8227-8231, 2006.
Lee, et al., "A comparison of the H2 sorption capacities of isostructural metal-organic frameworks with and without accessible metal sites: [{Zn2(abtc)(dmf)2}3] and [{Cu2(abtc)(dmf)2}3] versus [{Cu2(abtc)}3]", *Angew. Chem, Int. Ed.*, 47:7741-5, 2008.
Li et al., "Enhanced binding affinity, remarkable selectivity, and high capacity of $CO_2$ by dual functionalization of a rht-type metal-organic framework", *Angew. Chem. Int. Ed.*, 51:1412-1415, 2011.
Li et al., "Zeolitic imidazolate frameworks for kinetic separation of propane and propene", *J. Am. Chem. Soc.*, 131:10368-9, 2009.
Lin et al., "High H2 adsorption by coordination-framework materials", *Angew. Chem., Int. Ed.*, 45:7358-64, 2006.
Liu et al., "A high connectivity metal-organic framework with exceptional hydrogen and methane uptake capacities", *Chem. Sci.*, 3: 3032-3037, 2012.
Liu et al., "Engineering homochiral metal-organic frameworks for heterogeneous asymmetric catalysis and enantioselective separation" *Adv. Mater.*, 22:4112-35, 2010.
Llewllyn, et al., "High uptakes of $CO_2$ and $CH_4$ in mesoporous metal-organic frameworks MIL-100 and MIL-101", *Langmuir*, 24(14): 7245-50, 2008.
Lu, et al., "A highly porous and robust (3,3,4)-connected metal-organic framework assemble with a 90° bridging-angle embedded octoacarboxylate ligand", *Angew. Chem. Int. Ed.*, 51(7): 1580-4, 2012.

Ma et al., "A series of isoreticular chiral metal-organic frameworks as a tunable platform for asymmetric catalysis", *Nature Chem.*, 2:838, 2010.
Ma et al., "Preparation and gas adsorption studies of three mesh-adjustable molecular sieves with a common structure", *J. Am. Chem. Soc.*, 131:6445, 2009.
McKinlay et al., "Exceptional behavior over the whole adsorption-storage-delivery cycle for NO in porous metal organic frameworks", *J. Am. Chem. Soc.*, 130(31):10440-4, 2008.
Murray et al., "Highly-selective and reversible $O_2$ binding in $Cr_3(1,3,5-benzenetricarboxylate)_2$", *J. Am. Chem. Soc.*, 132:7856-7, 2010.
Nuzhdin et al., "Enantioselective chromatographic resolution and one-pot synthesis of enantiomerically pure sulfoxides over a homochiral Zn-organic framework", *J. Am. Chem. Soc.*, 129:12958-9, 2007.
Pakseresht, et al., "Equilibrium isotherms for CO, $CO_2$, $CH_4$, and $C_2H_4$ on the 5A molecular sieve by a simple volumetric apparatus", *Sep. Purif. Technol.*, 28: 53-60, 2002.
Peterson, et al, "Local vibrational mechanism for negative thermal expansion: a combined neutron scattering and first-principles study",*Angew. Chem. Int. Ed.*, 49:585-588, 2010.
Sircar and Golden, "Purification of hydrogen by pressure swing adsorption", *Sep. Sci. and Technol.*, 35:667-687, 2000.
Sun, et al., "An interweaving MOF with high hydrogen uptake", *J. Am. Chem. Soc.*, 128:3896-7, 2006.
Sun, et al, "Highly stable crystalline catalysts based on a microporous metal-organic framework and polyoxometalates", *J. Am. Chem. Soc.*, 131:1883, 2009.
Vaidhyanathan et al., "A family of nanoporous materials based on an amino acid backbone", *Angew. Chem., Int. Ed.*, 45:6495, 2006.
Wang et al., "Bottom-up synthesis of porous coordination frameworks: apical substitution of a pentanuclear tetrahedral precursor", *Angew. Chem., Int. Ed.*, 48:5291-5295, 2009.
Wang, et al., "A large-surface-area boracite-network-topology porous MOF constructed from a conjugated ligand exhibiting a high hydrogen uptake capacity", *Inorg. Chem.* 48:7519-21, 2009.
Wu, et al., "Cu-TDPAT, an rht-type dual-functional metal-organic framework offering significant potential for use in $H_2$ and natural gas purification processes operating at high pressures", *J. Phys. Chem. C..*, 116:16609, 2012.
Wu, et al., "Metal-organic frameworks with a three-dimensional ordered macroporous structure: dynamic photonic materials", *Angew. Chem. Int. Ed.*, 50:12518-22, 2011.
Xiang, et al "Microporous metal-organic framework with potential for carbon dioxide capture at ambient conditions", *Nat. Commun.*, 3:954, 2012.
Xiao, et al "High-capacity hydrogen and nitric oxide adsorption and storage in a metal-organic framework", *J. Am. Chem. Soc.*, 129:1203-1209, 2007.
Yan, et al., "Metal-organic polyhedral frameworks: high h(2) adsorption capacities and neutron powder diffraction studies", *J. Am. Chem. Soc.*, 132:4092, 2010.
Yuan, et al., "An isoreticular series of metal-organic frameworks with dendritic hexacalboxylate ligands and exceptionally high gas-update capacity", *Angew. Chem., Int. Ed.*, 49:5357, 2010.
Zhang et al., "Exceptional framework flexibility and sorption behavior of a multifunctional porous cuprous triazolate framework", *J. Am. Chem. Soc.*, 130:6010, 2008.
Zheng et al., "Enhanced $CO_2$ binding affinity of a high-uptake rht-type metal-organic framework decorated with acylamide groups", *J. Am. Chem. Soc.*, 133:748, 2011.

\* cited by examiner

Figure 1A-D

METAL-ORGANIC FRAMEWORKS FOR SELECTIVE SEPARATIONS

This application is a national phase application under 35 U.S.C. 371 of International Application No. PCT/US2014/014901, filed Feb. 5, 2014, which claims the benefit of U.S. Provisional Patent Application No. 61/761,592, filed on Feb. 6, 2013. The entire text of the above referenced disclosures is specifically incorporated herein by reference.

BACKGROUND OF THE INVENTION

I. Field of the Invention

The present disclosure relates generally to the fields of chemistry and materials science. More particularly, it concerns metal-organic frameworks, compositions thereof and methods use thereof, including for separating gas molecules, sensing, heterogeneous catalysis, drug delivery, lithium sulfide battery, membrane and analytical devices.

II. Description of Related Art

Microporous metal-organic frameworks (MOFs) have been rapidly emerging as new type of porous materials for gas storage, separation, sensing and heterogeneous catalysis. The tunable pores and the immobilized functional sites within such microporous MOFs have enabled them to direct specific recognition of certain molecules based upon size and functionality.

Precise control of pore sizes and pore surfaces within porous materials is very important for their highly selective recognition and thus separation of small molecules. The pores within such porous MOFs can be systematically modified simply by changing the secondary building blocks (SBUs), changing the organic bridging linkers and controlling the framework interpenetration (Deng et al., 2010; Chen et al., 2010; Ma et al., 2010; Horike et al., 2009). In fact, to systematically tune the micropores to induce their size specific encapsulation of small gas molecules, various series of microporous metal-organic framework materials have been emerging as the promising microporous media for the recognition and separation of small gas molecules (Kitaura et al., 2004; Chen et al., 2004; Cho et al., 2006; Liu et al., 2010; Murray et al., 2010; Ma et al., 2009; McKinlay et al., 2008; Dubbeldam et al., 2008; Chen et al., 2006; Finsy et al., 2008; Bae et al., 2010; Zhang et al., 2008; Dybtsev et al., 2004; Li et al., 2009; Vaidhyanathan et al., 2006; Nuzhdin et al., 2007; Dybtsev et al., 2006; Chen et al., 2008).

When considering the organic linkers, m-benzenedicarboxylate organic linkers in MOF play a crucial role in the realization of highly porous MOFs. In fact, this fundamental organic building unit can be incorporated into a great number of organic linkers with different aromatic backbones, leading to a variety of highly porous MOFs for gas storage and separation. (Chen, et al., 2005; Lin, et al., 2006; Lee, et al., 2008; Hu, et al., 2009; Farha, et al., 2010; Yuan, et al., 2010; Yan, et al., 2010; Li, et al., 2011; Zheng, et al., 2011; Guo, et al., 2011; Liu, et al., 2012; Farha, et al., 2012) Recently, the two porous MOFs with BET surface area over 7000 $m^2/g$ have been targeted from two hexacarboxylate organic linkers build from three m-benzenedicarboxylate units in Farha, et al., 2012, which is incorporated herein by reference. The introduction of the multivalent ligand by modifying the connection point of the chelating ligand provides the flexibility to augment the pore size of the MOF through systematic modification of the organic linkers. The systematic modification allows for the selective incorporation of different gas molecules based upon the linkers and the resultant pore size.

Motivated by the power of the m-benzenedicarboxylate organic building unit to construct highly porous MOFs, work has been done to expand the organic units as shown in FIG. 1(a) (middle and right ones), for the design of new organic linkers and thus porous MOFs through their self-assembly with the paddle-wheel $Cu_2(CO_2)_4$ SBUs. Such expanded organic units have never been utilized before to create porous MOFs.

SUMMARY OF THE INVENTION

In some aspects, the invention provides a metal-organic framework (MOF) comprising a repeat unit of the formula $[Cu_3(L)_2(H_2O)_3]$, wherein L is a ligand of the formula or a protonated form thereof:

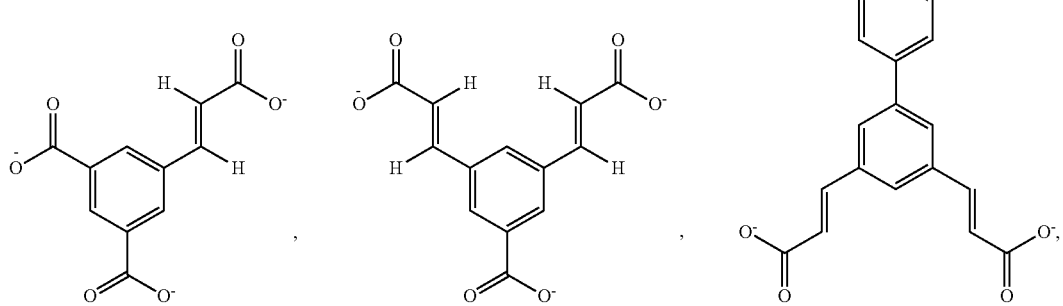

3
-continued
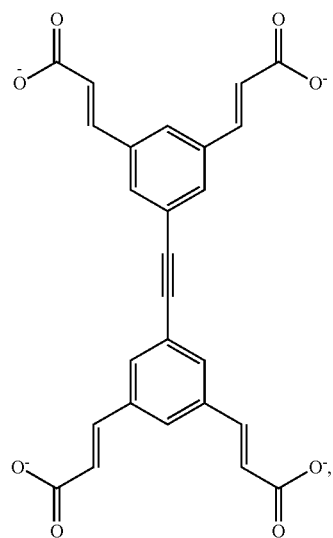 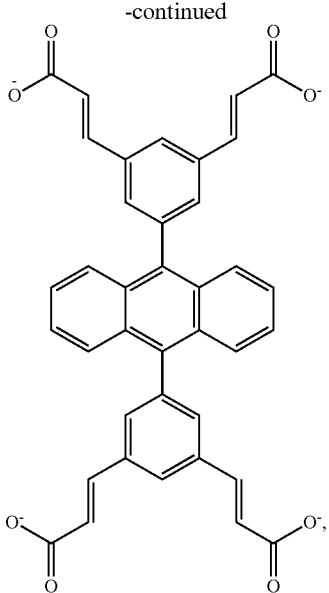 
4
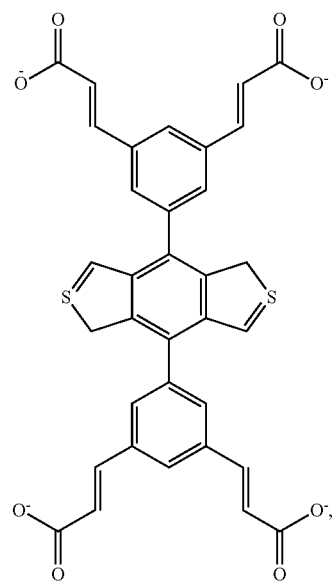
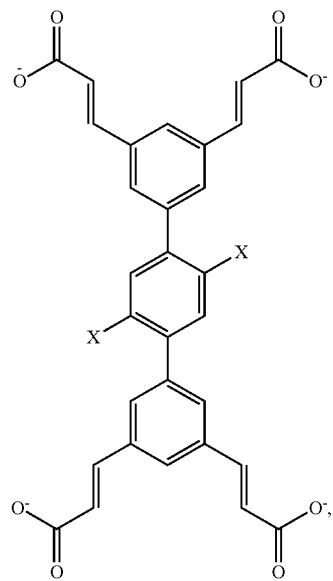

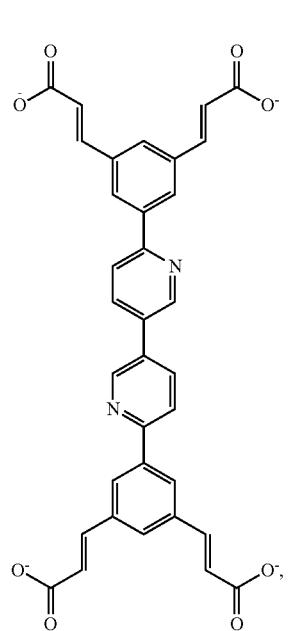
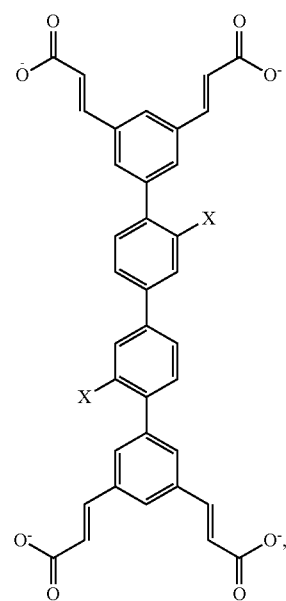
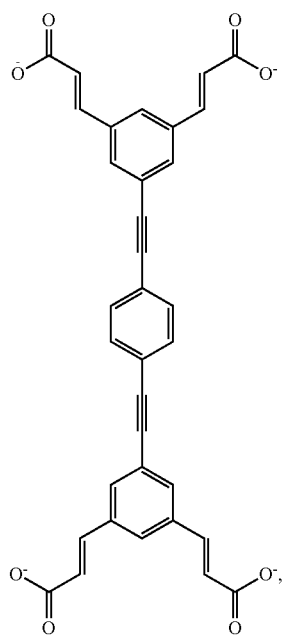
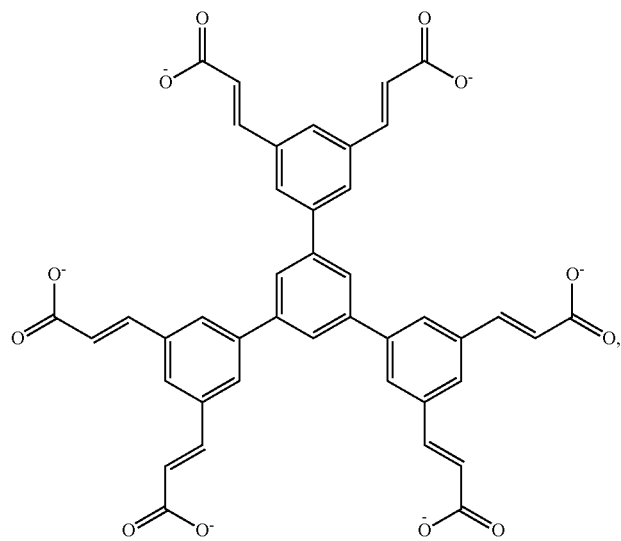

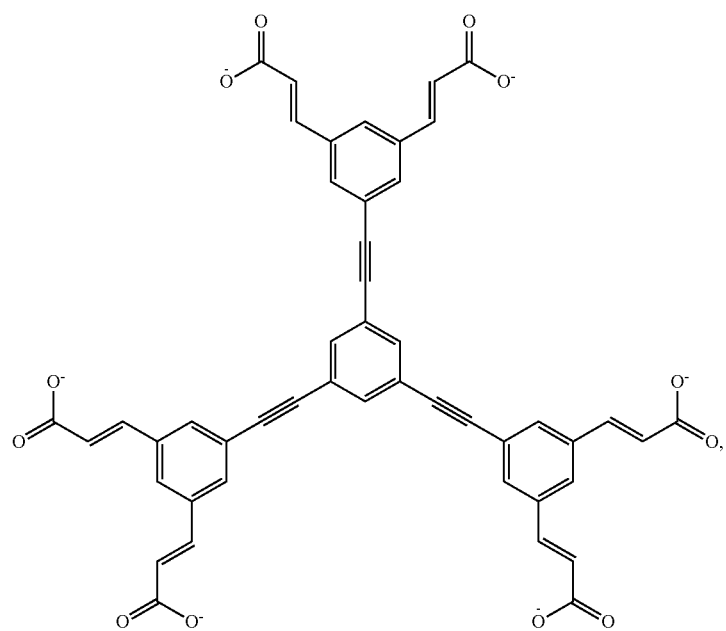
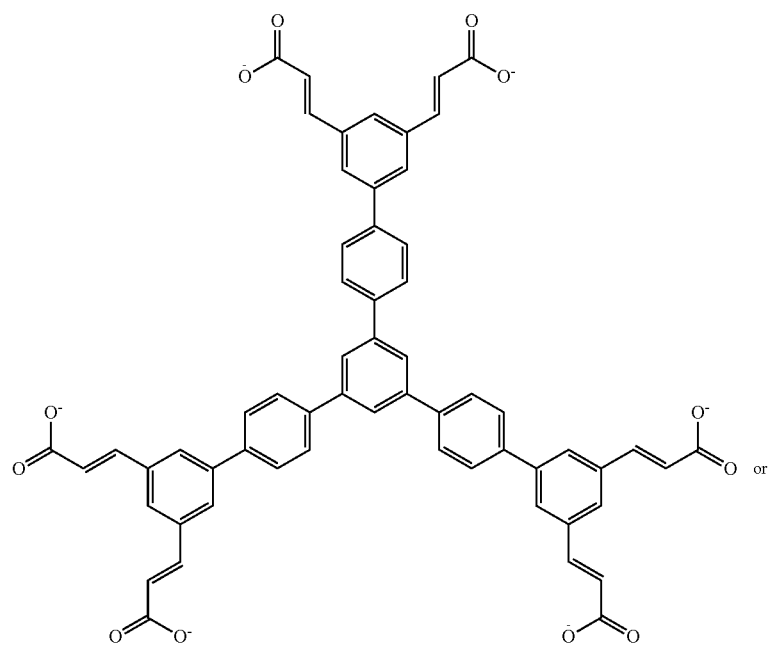
or

-continued

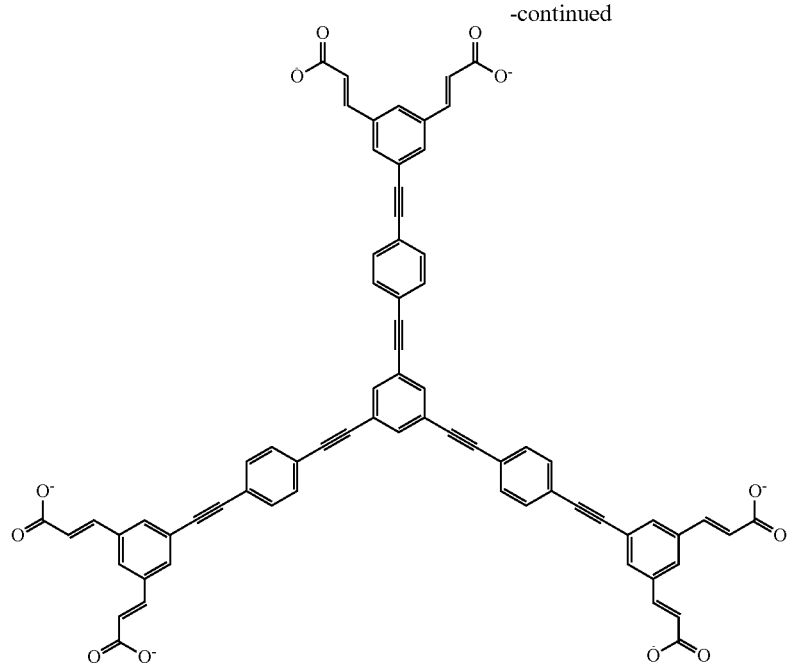

wherein, X is selected independently from —OH, —F, —Cl, —Br, —I, —NH$_2$, —NO$_2$, —CO$_2$H, —CO$_2$CH$_3$, —CO$_2$CH$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$OH or —S(O)$_2$NH$_2$.

In some embodiments, the metal-organic framework (MOF) comprises a repeat unit of the formula [Cu$_3$(L1)$_2$(H$_2$O)$_3$] or [Cu$_3$(L2)$_2$(H$_2$O)$_3$], wherein L1 is a ligand of the formula:

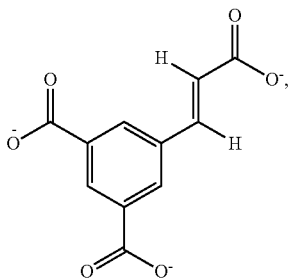

and
wherein L2 is a ligand of the formula:

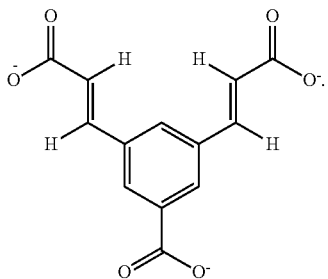

In some embodiments, the metal organic framework is activated for sorption of gas molecules. In some embodiments, the MOF further comprises one or more than one type of guest molecule. In some embodiments, the guest molecule is a solvent molecule. In some embodiments, the solvent molecule is water. In other embodiments, the solvent molecule is N,N'-dimethylformamide.

In some embodiments, the MOF further comprises about two N,N'-dimethylformamide and five and half water molecules per repeat unit. In other embodiments, the MOF is further comprised of about five N,N'-dimethylformamide and six and half water molecules per repeat unit. In some cases, the solvent molecules occupy the pores of the MOF.

In some embodiments, one type of guest molecule is a gas molecule. In some cases, the gas molecule is H$_2$, CO$_2$, or CH$_4$. In some embodiments, the gas molecule is CO$_2$. In some embodiments, the gas molecule is CH$_4$. In other embodiments, the gas molecule is H$_2$. In other cases, the gas molecule is CO$_2$ and CH$_4$.

In some instances, MOF is substantially free of solvent molecules.

In some cases, the MOF has a weight percentage at least 90% attributable to repeat units of the formula [Cu$_3$(L1)$_2$(H$_2$O)$_3$] or [Cu$_3$(L2)$_2$(H$_2$O)$_3$]. In other cases, the MOF has a weight percentage at least 95% attributable to repeat units of the formula [Cu$_3$(L1)$_2$(H$_2$O)$_3$] or [Cu$_3$(L2)$_2$(H$_2$O)$_3$]. In some cases, the MOF has a weight percentage at least 99% attributable to repeat units of the formula [Cu$_3$(L1)$_2$(H$_2$O)$_3$] or [Cu$_3$(L2)$_2$(H$_2$O)$_3$]. In other instances, the metal-organic framework has been adhered to a fixed surface.

In some embodiments, the repeat unit of the MOF is a ligand of the formula listed in Example IV Additional Ligands.

In another aspect, the invention provides methods of separating two or more compounds using an MOF comprising:

(a) obtaining a metal-organic framework (MOF) comprising a repeat unit of the formula [Cu$_3$(L1)$_2$(H$_2$O)$_3$] or [Cu$_3$(L2)$_2$(H$_2$O)$_3$], wherein L1 is a ligand of formula:

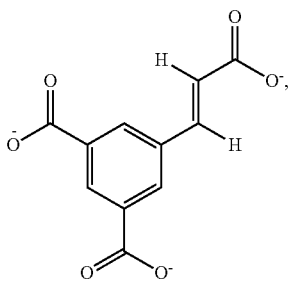

and
L2 is a ligand of formula:

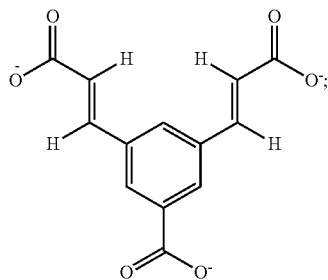

(b) combining the MOF with a mixture comprising a first compound and one or a group of second compounds; and (c) separating the one or more compounds based on their differential sorption rate within the MOF.

In some embodiments, the molecules separated are gas molecules. In some cases, the first compound is $H_2$. In some cases, the second compound is $CH_4$ or $CO_2$. In other cases, the second compound is $CH_4$ and $CO_2$. In some cases, the second compound is $CH_4$ and $CO_2$ and the first compound is $H_2$.

In some embodiments, the separation is carried out at high pressure. In some cases, the separation is carried out at pressures above 2 mPa. In some embodiments, the separation is carried out at pressures above 4 mPa.

In some embodiments, the MOF is attached to a fixed bed surface. In some embodiments, the MOF further comprises an absorber. In some embodiments, the absorption is carried out at any temperature. In other embodiments, the absorption is carried out at room temperature.

In other aspect, the invention provides methods of using the MOFs provided herein for sensing, heterogeneous catalysis, drug delivery, and a component of, for example, a lithium sulfide battery, a membrane, and/or an analytical device.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIG. 1A shows the m-benzenedicarboxylate organic building unit (left) and two new expanded ones (middle and right); FIGS. 1B-1D show the self-assembly of (B) $H_3BTC$ and (C-D) two new organic linkers with paddle-wheel $Cu_2(CO_2)_4$ unit lead to the construction of isoreticular porous MOFs whose pores (spheres highlighted by black arrows) are systematically enlarged (Cu, dark gray polyhedra; C, light gray tubes; 0, small dark gray spheres surrounding the polyhedra; H atoms are omitted for clarity) for MOF, ZJU-35 and ZJU-36, respectively.

DESCRIPTION OF ILLUSTRATIVE EMBODIMENTS

Figure 1:
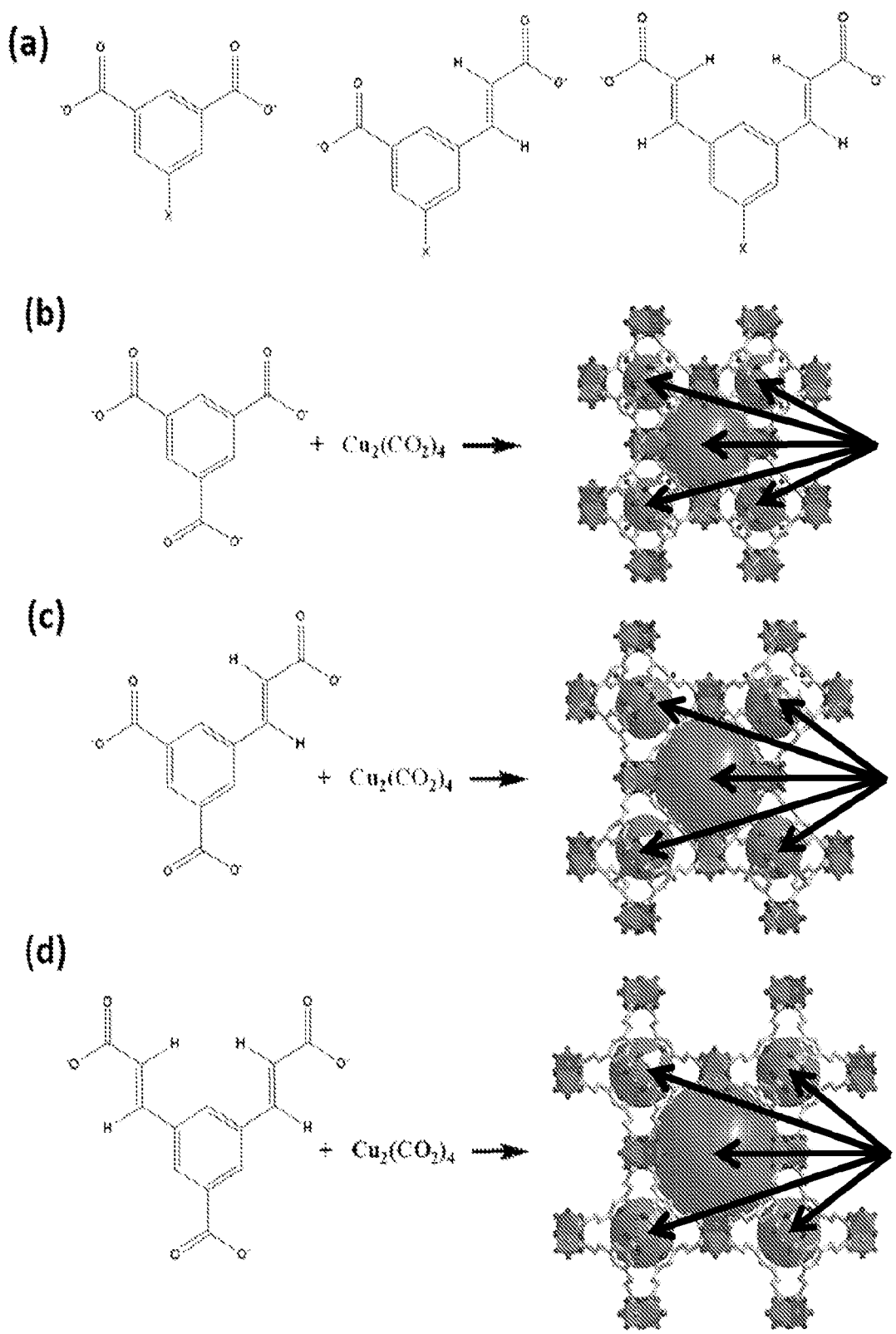
FIGS. 1A-D show the organic components of the MOF and the size and shape of the corresponding pores within the structure.

Disclosed herein are metal-organic frameworks based upon an organic ligand derivative of m-benzenetricarboxylate. Theses MOFs made be used to selective purify hydrogen gas from production byproducts, $CO_2$ and $CH_4$. These MOFs can also be used in applications towards sensing, heterogeneous catalysis, drug delivery, lithium sulfide battery, membrane and analytical devices through the manner taught by Xiao, 2007, Sun, 2009, Guo, 2009, Peterson, 2010 and Wu 2011, which are incorporated herein by reference.

I. Definitions

ZJU-35 corresponds to the formula $[Cu_3(L1)_2(H_2O)_3](G)_x$, wherein G is a guest molecule, and L1 is a m-benzenetricarboxylate derivative.

ZJU-36 corresponds to the formula $[Cu_3(L2)_2(H_2O)_3](G)_x$, wherein G is a guest molecule, and L2 is a m-benzenetricarboxylate derivative.

DMF refers to N,N'-dimethylformamide.

"Guest molecule," or "G" in the context of a chemical formula, refers to a molecule, including a solvent molecule or a gas molecule, that is enclosed within the pores or open sites of a framework material such as an MOF or M'MOF.

Examples of guest molecules include, for example, methane, water, N,N'-dimethylformamide, N,N'-diethylformamide, ethanol and nitrobenzene.

"Metal-organic frameworks" (MOFs) are framework materials, typically three-dimensional, self-assembled by the coordination of metal ions with organic linkers exhibiting porosity, typically established by gas adsorption. The MOFs discussed and disclosed herein are at times simply identified by their repeat unit (see below), that is without brackets or the subscript n. A mixed-metal-organic frameworks (M'MOF) is a subset of MOFs having two of more types of metal ions.

A "repeat unit" is the simplest structural entity of certain materials, for example, frameworks and/or polymers, whether organic, inorganic or metal-organic. In the case of a polymer chain, repeat units are linked together successively along the chain, like the beads of a necklace. For example, in polyethylene, —[—CH$_2$CH$_2$—]$_n$—, the repeat unit is —CH$_2$CH$_2$—. The subscript "n" denotes the degree of polymerisation, that is, the number of repeat units linked together. When the value for "n" is left undefined, it simply designates repetition of the formula within the brackets as well as the polymeric and/or framework nature of the material. The concept of a repeat unit applies equally to where the connectivity between the repeat units extends into three dimensions, such as in metal organic frameworks, cross-linked polymers, thermosetting polymers, etc. Note that for MOFs the repeat unit may also be shown without the subscript n.

"Pores" or "micropores" in the context of metal-organic frameworks are defined as open space within the MOFs; pores become available, when the MOF is activated for the storage of gas molecules. Activation can be achieved by heating, e.g., to remove solvent molecules.

"Multimodal size distribution" is defined as pore size distribution in three dimensions.

"Interpenetrating metal-organic framework" is defined as metal-organic frameworks interlocked with one another.

"Multidentate organic linker" is defined as ligand having several binding sites for the coordination to one or more metal ions.

When used in the context of a chemical group, "hydrogen" means —H; "hydroxy" means —OH; "oxo" means =O; "halo" means independently —F, —Cl, —Br or —I; "amino" means —NH$_2$, and "nitro" means —NO$_2$.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤n)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10, or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

Any undefined valency on an atom of a structure shown in this application implicitly represents a hydrogen atom bonded to the atom. When a group "R" is depicted as a "floating group" on a ring system, for example, in the formula:

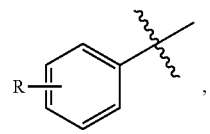

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

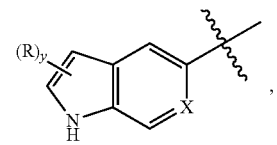

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

The term "alkane" when used without the "substituted" modifier refers to a non-aromatic hydrocarbon consisting only of saturated carbon atoms and hydrogen and having a linear or branched, cyclo, cyclic or acyclic structure. Thus, as used herein cycloalkane is a subset of alkane. The compounds CH$_4$ (methane), CH$_3$CH$_3$ (ethane), CH$_3$CH$_2$CH$_3$ (propane), (CH$_2$)$_3$ (cyclopropane), CH$_3$CH$_2$CH$_2$CH$_3$ (n-butane), and CH$_3$CH(CH$_3$)CH$_3$ (isobutane), are non-limiting examples of alkanes. A "substituted alkane" differs from an alkane in that it also comprises at least one atom independently selected from the group consisting of N, O, F, Cl, Br, I, Si, P, and S. Some non-limiting examples of groups which can replace an atom on the alkane include —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following compounds are non-limiting examples of substituted alkanes: CH$_3$OH, CH$_3$Cl, nitromethane, CF$_4$, CH$_3$OCH$_3$ and CH$_3$CH$_2$NH$_2$.

The term "arene" when used without the "substituted" modifier refers to an hydrocarbon having at least one six-membered aromatic ring. One or more alkyl, alkenyl or alkynyl groups may be optionally attached to this ring. Also this ring may optionally be fused with other rings, including non-aromatic rings. Benzene, toluene, naphthalene, and biphenyl are non-limiting examples of arenes. A "substituted arene" differs from an arene in that it also comprises at least one atom independently selected from the group consisting of N, O, F, Cl, Br, I, Si, P, and S. Some non-limiting examples of groups which can replace an atom on the alkane include —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Phenol, 6-chlorobenzene, and nitrobenzene are non-limiting examples of substituted arenes.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Any undefined valency on a carbon atom of a structure shown in this application implicitly represents a hydrogen atom bonded to the atom.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

The term "saturated" when referring to an atom means that the atom is connected to other atoms only by means of single bonds.

The above definitions supersede any conflicting definition in any of the reference that is incorporated herein by reference. The fact that certain terms are defined, however, should not be considered as indicative that any term that is undefined is indefinite. Rather, all terms used are believed to describe the invention in terms such that one of ordinary skill can appreciate the scope and practice the present invention.

II. Synthetic Methods

Disclosed herein are the synthesis, structures, and sorption studies of two new MOFs, [Cu$_3$(L1)$_2$(H$_2$O)$_3$].2DMF.5.5H$_2$O (ZJU-35) and [Cu$_3$(L2)$_2$(H$_2$O)$_3$].5DMF.6.5H$_2$O (ZJU-36). As shown in the schemes below, the two new tricarboxylate organic linkers 5-(2-carboxyvinyl)isophthalic acid (H$_3$L1) and 3,3'-(5-carboxy-1,3-phenylene)diacrylic acid (H$_3$L2) were simply synthesized by Heck cross-coupling reactions of methylated bromo-phenylcarboxylate and methyl acrylate, followed by hydrolysis and acidification.

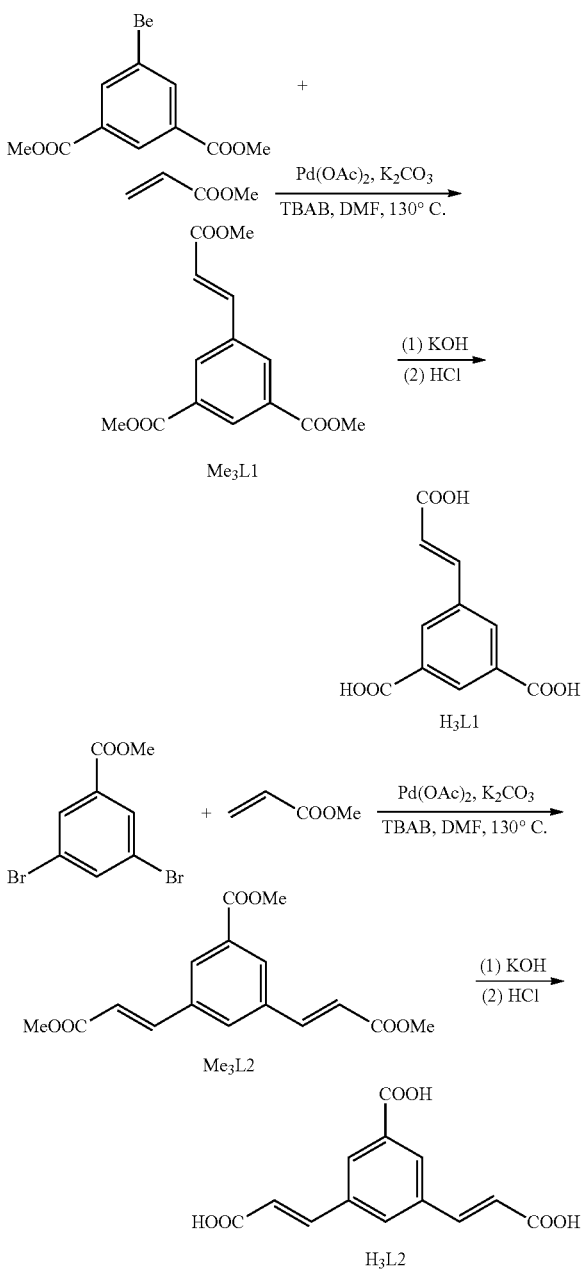

Reactions of these two linkers with Cu(NO$_3$)$_2$.3H$_2$O in acidified DMF/H$_2$O at 65° C. for two days afforded blue crystals of ZJU-35 and ZJU-36, respectively. The compositions of the as-synthesized MOFs were based on the elemental analysis, thermogravimetric analysis (TGA) and single crystal structure.

Single crystal X-ray diffraction analysis revalued that the two MOFs are isomorphous, which crystallize in the cubic Fm-3m space group. Both ZJU-35 and ZJU-36 are isoreticular with the very important prototype MOF HKUST-1 of the tbo topologies, although the new linkers $H_3L1$ and $H_3L2$ are apparently less symmetric than $H_3BTC$. It has been rationalized that the self-assembly of tricarboxylate with paddle-wheel $Cu_2(CO_2)_4$ either forms tbo or pto frameworks which are attributed to the different structural orientation of tritopic carboxylates taught in Chen, et al., 2001, Furukawa, et al., 2011, Sun et al., 2006, and Wang et al., 2009, which are incorporated herein by reference. Because the $H_3L1$ and $H_3L2$ are larger than $H_3BTC$, the pores within these isoreticular MOFs are systematically enlarged: the small pockets are 5.3, 6.4 and 7.5 Å, and the large cages are 10.8, 14.4 and 16.5 Å in HKUST-1, ZJU-35 and ZJU-36, respectively, taken in account of the van der Waals radius, as shown in FIG. 1. PLATON calculations indicate that the void spaces are 62.3% and 76.9% for ZJU-35 and ZJU-36, respectively.

Figure 2:
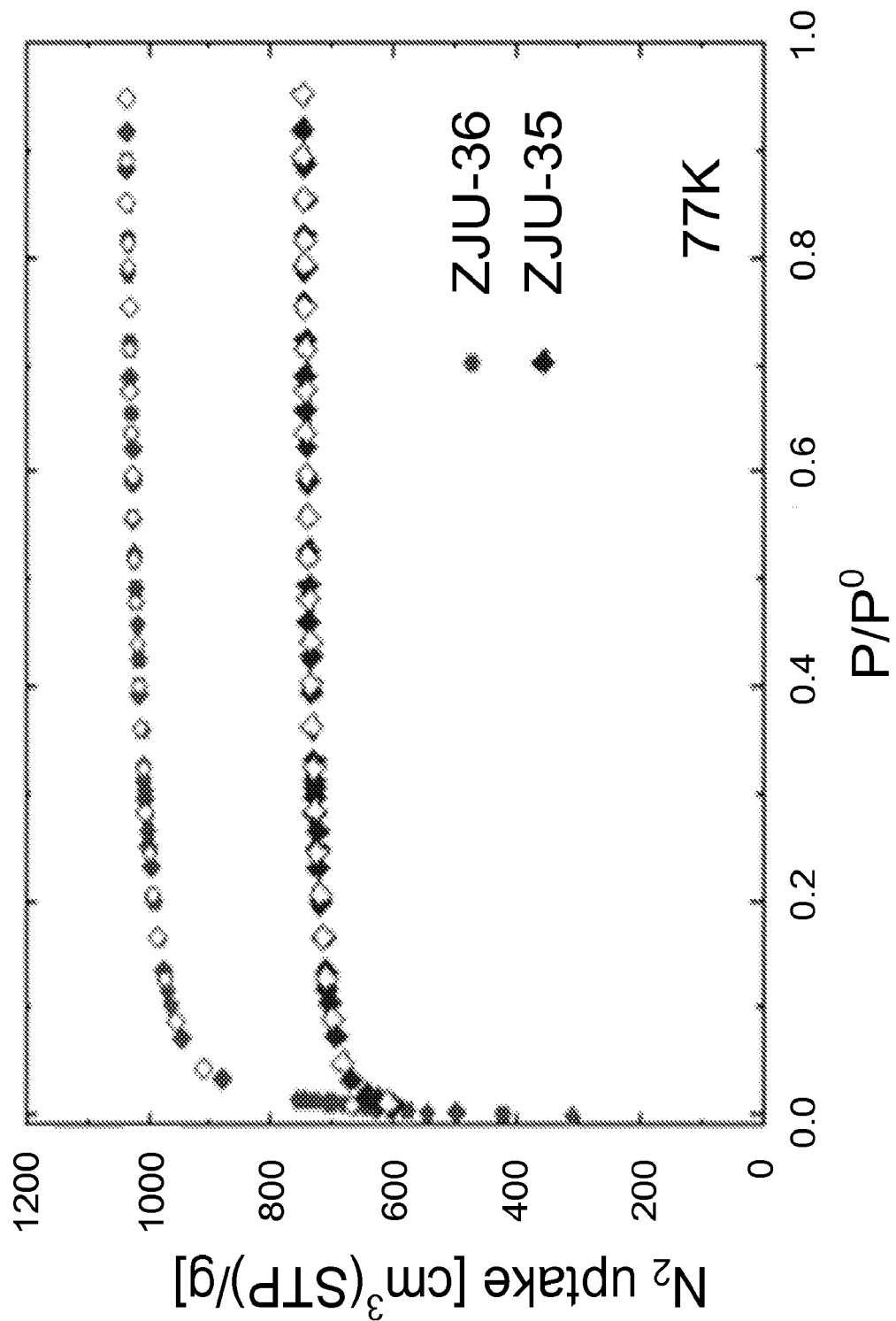
FIG. 2 shows the $N_2$ sorption isotherms of ZJU-35 and ZJU-36 at 77 K.
Figure 3A:
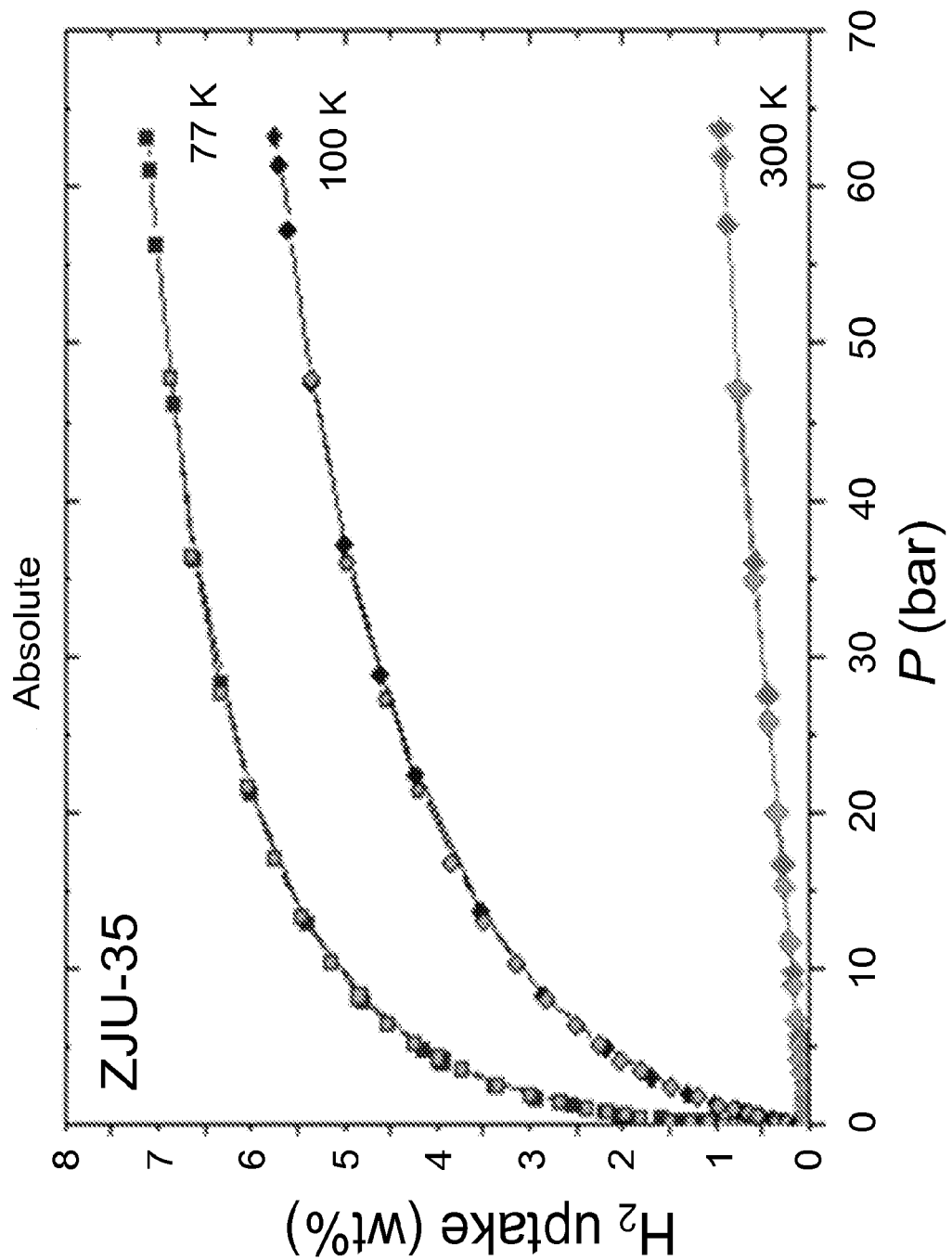
FIGS. 3A-B show $H_2$ (absolute) sorption isotherms of ZJU-35 (A) and ZJU-36 (B) at different temperatures.
Figure 3B:
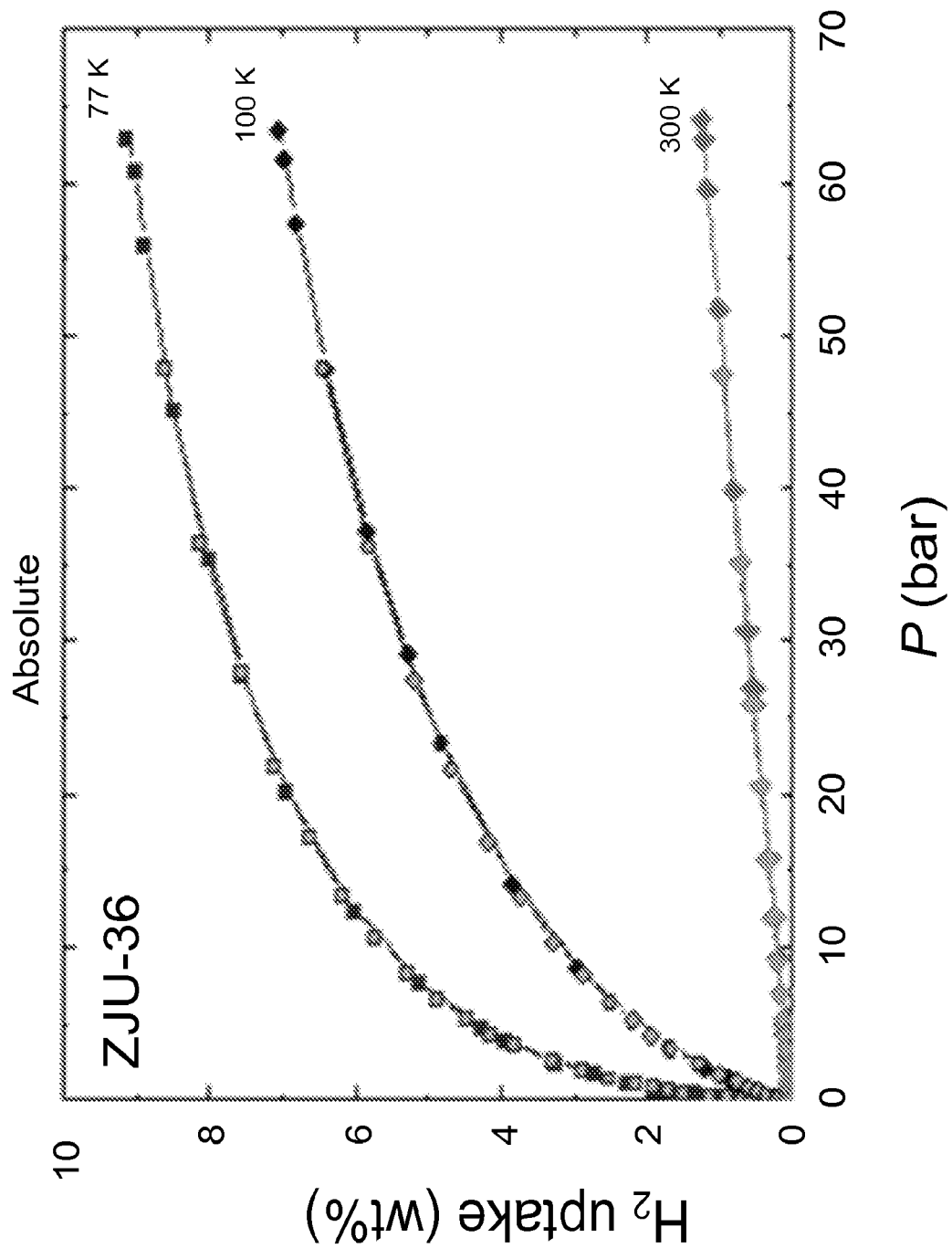
Figure 4:
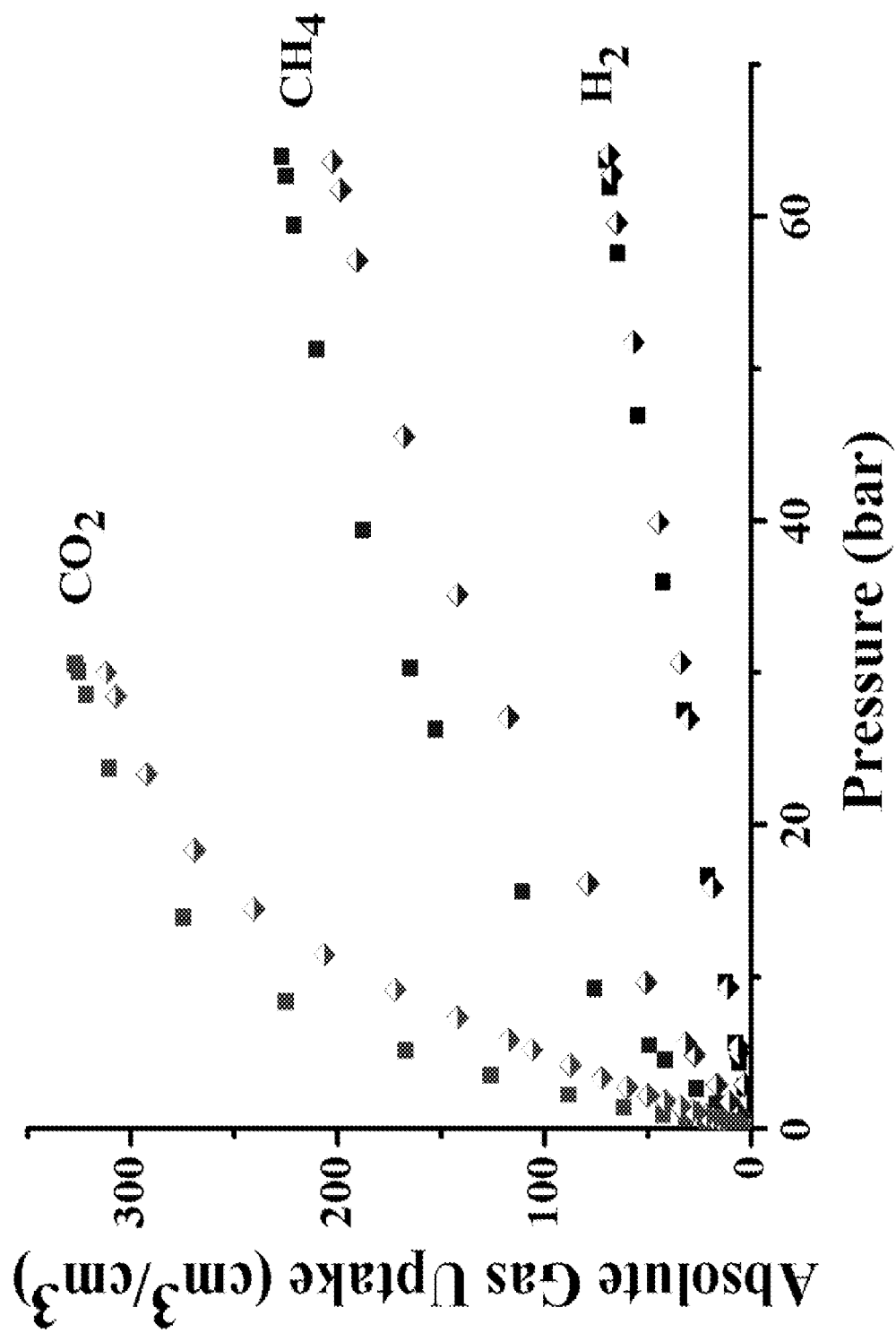
FIG. 4 shows the absolute gas sorption isotherms of $CO_2$ (top), $CH_4$ (middle) and $H_2$ (bottom) of ZJU-35a (solid square) and ZJU-36a (open solid diamond) at 300 K.

The acetone-exchanged ZJU-35 was outgassed at room temperature for 24 hours and followed at 373 K for 24 hours under high vacuum to yield activated ZJU-35a, while ZJU-36a was generated by activation of the acetone-exchanged ZJU-36 under high vacuum at room temperature for 24 hours and then at 353 K for 24 hrs. Both activated ZJU-35a and ZJU-36a exhibit type I reversible sorption isotherms and take up $N_2$ of 747 and 1033 $cm^3/g$ at 77 K and 1 bar, respectively (FIG. 2). Accordingly, ZJU-35a has BET surface area of 2958 $m^2/g$ and a pore volume of 1.156 $cm^3/g$, while ZJU-36a has BET surface area of 3243 $m^2/g$ and a pore volume of 1.599 $cm^3/g$. The porosities of both ZJU-35a and ZJU-36a are systematically higher than those of HKUST-1 with BET surface area of 1502 $m^2/g$ and a pore volume of 0.76 $cm^3/g$, and among the few percentage of highly porous MOFs. The maximum excess $H_2$ uptakes of ZJU-35a and ZJU-36a are 5.2 and 6.2 wt %, respectively, which correlate well with their corresponding surface areas. Their absolute $H_2$ storage capacities are 7.1 and 9.1 wt %, respectively, at 77 K and 63 bar, which are moderately high (FIG. 3A-B). Their room temperature absolute hydrogen storage are 1.0 and 1.2 wt %, respectively, for ZJU-35a and ZJU-36a. The $CH_4$ storage capacities of ZJU-35a and ZJU-36a are 227 and 203 $cm^3/cm^3$, respectively, at 300 K and 64 bar. The most interesting and important feature of ZJU-35a and ZJU-36a are their high $CO_2$ uptakes of 328 and 311 $cm^3/cm^3$, respectively, at 300 K and 30 bar (FIG. 4). In fact, ZJU-35a has the highest volumetric $CO_2$ uptake among any reported porous MOFs at 300 K and 30 bar (Table 1). The interplay of the suitable pore spaces and framework density has enabled ZJU-35a as a very promising material for precombustion $CO_2$ capture (hydrogen purification) and related separation.

TABLE 1

Comparison of Some Examined Porous Metal-Organic Frameworks for their High Pressure $CO_2$ Uptake at Room Temperature and 30 Bar.

| MOFs | BET ($m^2/g$) | $V_p$ ($cm^3/g$) | $D_c$ ($g/cm^3$) | $CO_2$ uptake |
|---|---|---|---|---|
| ZJU-35 | 2958 | 1.156 | 0.657 | 328 $cm^3/cm^3$ |
| ZJU-36 | 3243 | 1.599 | 0.496 | 311 $cm^3/cm^3$ |
| PCN-61 (Yuan, et al, 2010) | 3000 | 1.36 | 0.56 | 317 $cm^3/cm^3$ |
| PCN-66 (Yuan, et al, 2010) | 4000 | 1.63 | 0.45 | 281 $cm^3/cm^3$ |
| PCN-68 (Yuan, et al, 2010) | 5109 | 2.13 | 0.38 | 276 $cm^3/cm^3$ |
| PCN-80 (Lu, et al, 2012) | 3584 | 1.47 | 0.574 | 212 $cm^3/cm^3$ |
| MIL-100 (Latroche, et al, 2006, Llewellyn, et al., 2008) | 1900 | 1.10 | 0.70 | 237 $cm^3/cm^3$ |
| MIL-101b (Latroche, et al, 2006, Llewellyn, et al., 2008) | 3780 | 1.74 | 0.44 | 248 $cm^3/cm^3$ |
| MIL-101c (Llewellyn, et al., 2008) | 4230 | 2.15 | 0.44 | 276 $cm^3/cm^3$ |
| MOF-5 (Kaye, et al., 2007) | 3800 | 1.55 | 0.59 | 251 $cm^3/cm^3$ |
| MOF-17 (Furukawa, et al., 2010) | 4500 | 1.89 | 0.427 | 284 $cm^3/cm^3$ |
| MOF-200 (Furukawa, et al., 2010) | 4530 | 3.59 | 0.22 | 171 $cm^3/cm^3$ |
| MOF-205 (Furukawa, et al., 2010) | 4460 | 2.16 | 0.38 | 283 $cm^3/cm^3$ |
| MOF-210 (Furukawa, et al., 2010) | 6240 | 3.60 | 0.25 | 190 $cm^3/cm^3$ |
| DUT-9 (Gedrich, et al., 2010) | na | 2.18 | 0.358 | 293 $cm^3/cm^3$ |
| DUT-25 (Grünker, et al., 2012) | 4670 | 2.22 | 0.416 | 273 $cm^3/cm^3$ |
| NU-100 (Farha, et al., 2010) | 6143 | 2.82 | 0.279 | 253 $cm^3/cm^3$ |
| UTSA-20 (Guo, et al., 2011) | 1156 | 0.63 | 0.910 | 293 $cm^3/cm^3$ |
| Cu-TDPAT (Li, et al., 2011) | 1938 | 0.93 | 0.782 | 279 $cm^3/cm^3$ |

All references included in Table 1 are incorporated herein by reference.

Further details related to the syntheses and characterization of these MOFs is provided in the Examples section below. The methods described herein can be further modified, optimized and scaled up using the principles and techniques of chemistry and/or materials science as applied by a person skilled in the art. Such principles and techniques are taught, for example, in Chen et al. (2005), which is incorporated herein by reference.

III. Properties and Uses of MOFs

The high $CO_2$ and moderately high $CH_4$ uptakes of ZJU-35a and ZJU-36a motivated the examination of their applications on the $H_2$ purification under high pressure and room temperature. Hydrogen is commonly generated by steam-reforming of methane. This process generates CO and $H_2$, that is converted by the water-gas shift reaction to generate $CO_2$ and more $H_2$. For production of $H_2$, significant amounts of $CO_2$ (15-30%) need to be removed, along with relatively smaller amounts of $CH_4$ (5-20%) at pressures that often exceed 3 MPa. (Herm, et al., 2011, Herm, et al., 2012a, Herm, et al., 2012b, Wu, et al., 2012, He, et al., 2013) 50 Million tons of $H_2$ are synthesized and purified annually. The PSA processes are commonly designed to produce $H_2$ at purity levels ranging from 98-99.99%. (Sircar and Golden, 2000) The commonly used adsorbents in industry are activated carbon, LTA-5A, and NaX zeolites. Hydrogen purification is one industrial process for which optimized adsorbents are urgently needed because small improvements can result in significant energy savings and cost reductions.

Figure 5:
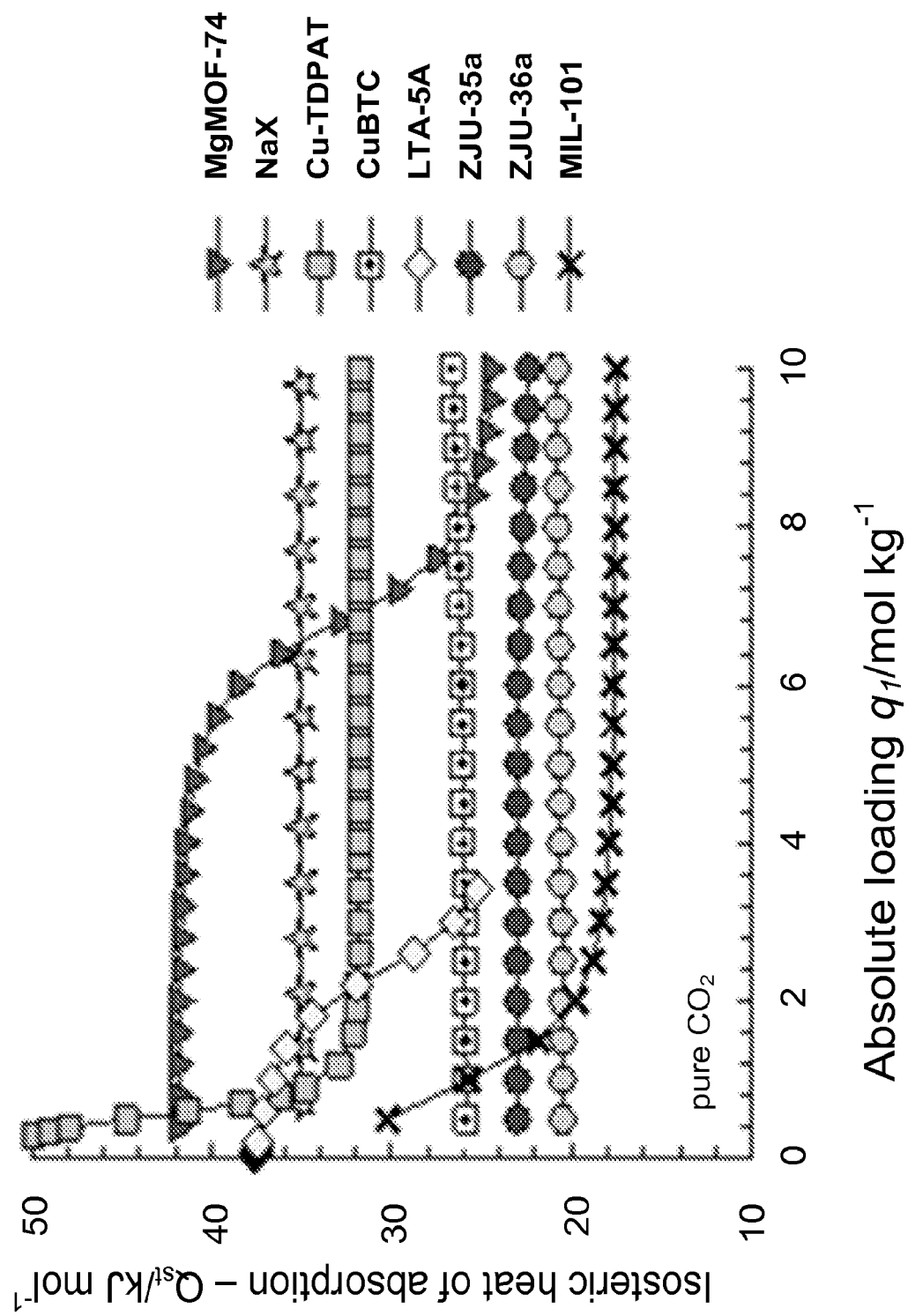
FIG. 5 shows the comparison of isosteric heats of adsorption, $Q_{st}$, of $CO_2$ in ZJU-35a, ZJU-36a, CuBTC (HKUST-1), MgMOF-74, Cu-TDPAT, MIL-101, NaX, and LT-5A. The calculations of $Q_{st}$ are based upon the Clausius-Clapeyron equation.
Figure 6A:
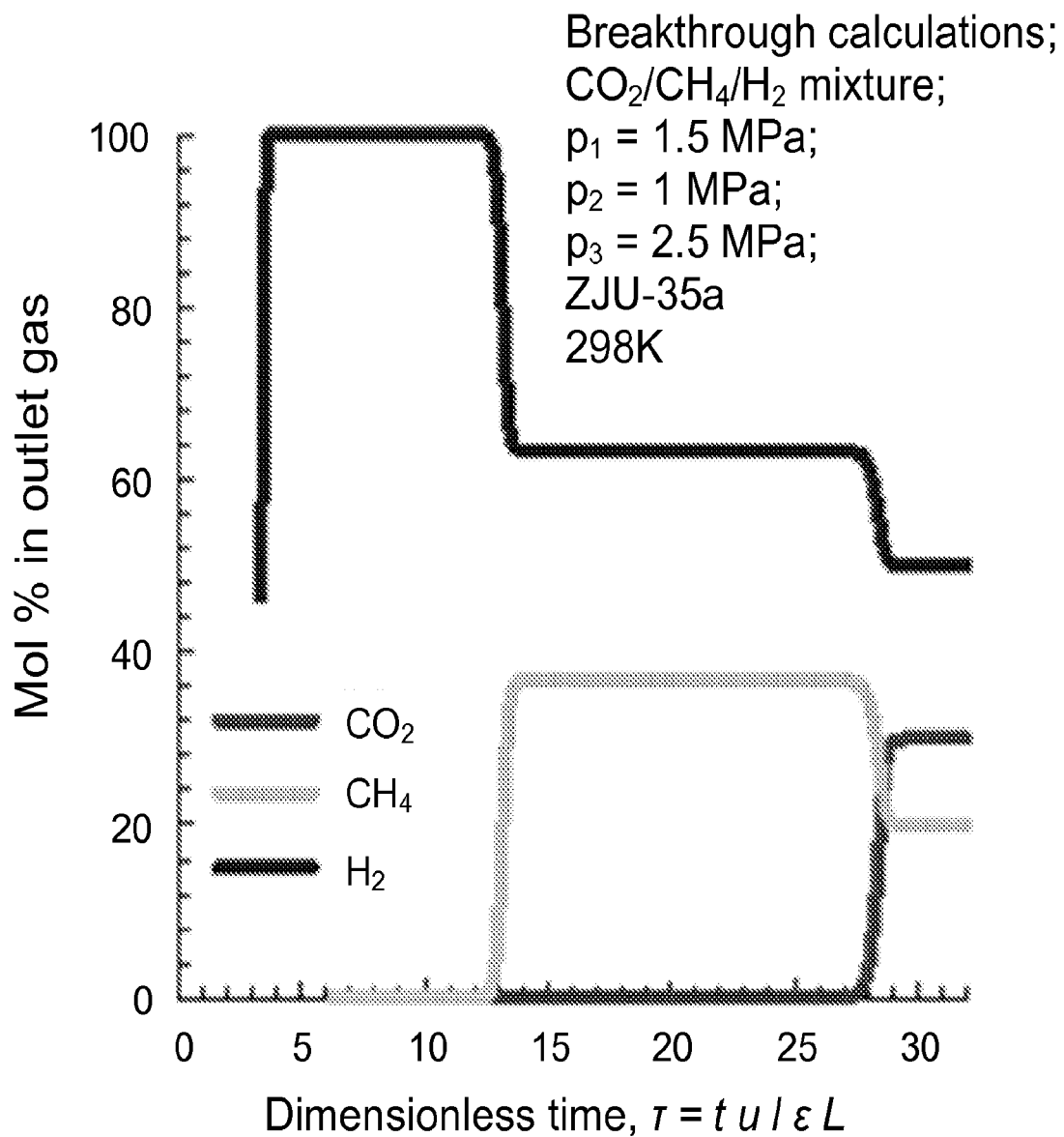
FIGS. 6A-B show the breakthrough characteristics of an adsorber packed with ZJU-35a (A) and ZJU-36a (B) maintained at isothermal conditions at 298 K and 5 MPa.
Figure 6B:
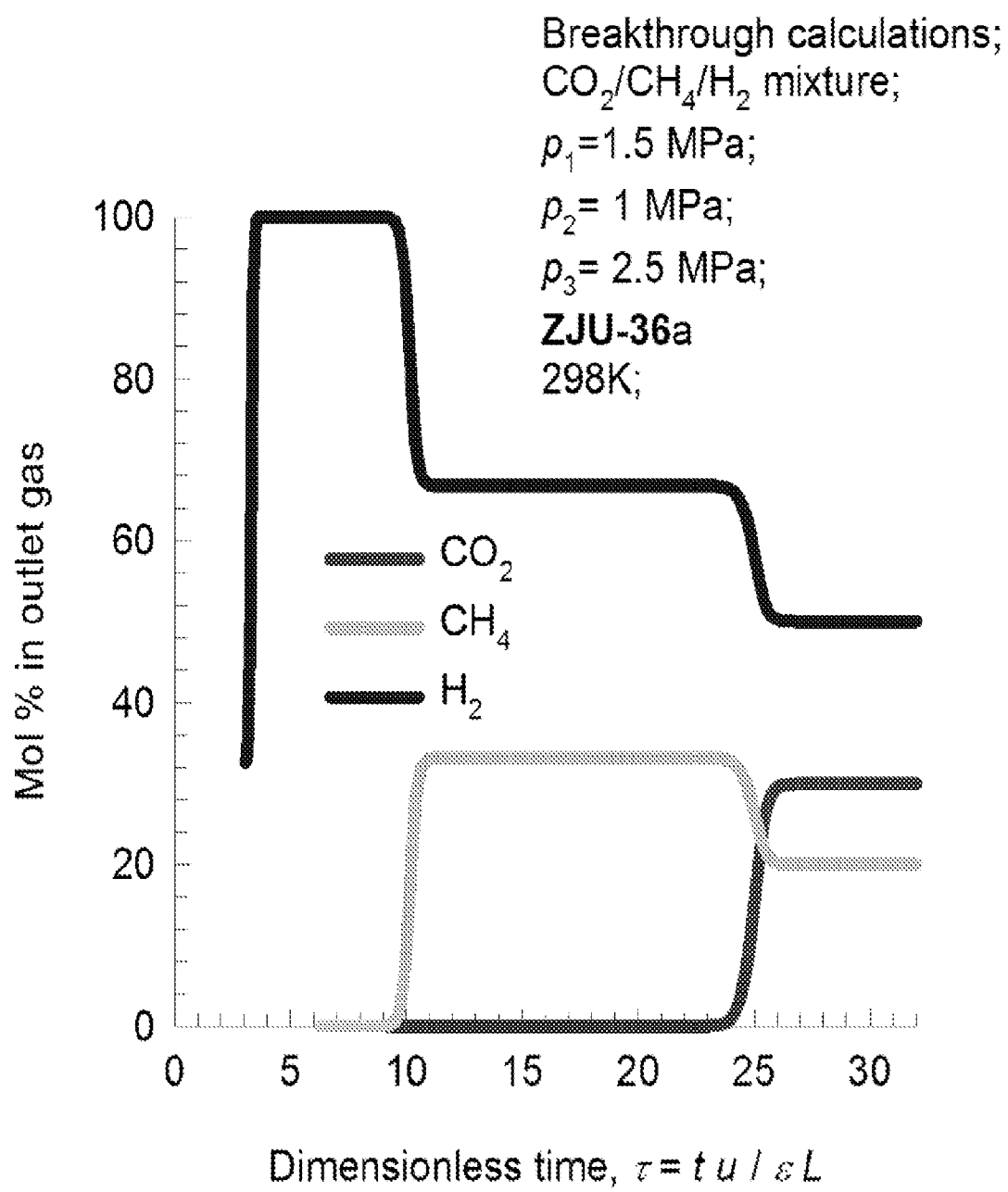

To establish the feasibility of ZJU-35a and ZJU-36a for high pressure PSA purification of hydrogen, their isosteric heats of adsorption, $Q_{st}$, of $CO_2$, adsorption selectivity, packed bed adsorber breakthrough simulation for a ternary 30/20/50 $CO_2/CH_4/H_2$ gas mixture, which is typically encountered in $H_2$ purification processes, were studied in detail and compared their performances with those examined porous MOFs (CuBTC (HKUST-1), MgMOF-74, Cu-TDPAT and MIL-101), zeolites (NaX and LTA-5A). (Herm, et al., 2011; Herm, et al., 2012; Wu, et al., 2012) As shown in FIG. 6, the $Q_{st}$ values of $CO_2$ systematically decrease from HKUST-1 to ZJU-35a and then to ZJU-36a because the pores are enlarged while the open metal site densities are reduced gradually within these isoreticular MOFs. Cu-TD-PAT has very high $Q_{st}$ values of $CO_2$, particularly at low loading of $CO_2$, because of its amine groups on the pore surfaces for their very strong interactions with $CO_2$. The very large $Q_{st}$ values of $CO_2$ for MgMOF-74 are attributed to the strong electrostatic interactions between open $Mg^{2+}$ sites and $CO_2$ molecules. Zeolites NaX and LTA-5A with smaller pores have larger $Q_{st}$ values of $CO_2$ than ZJU-35a and ZJU-36a. The interactions between MIL-101 and $CO_2$ molecules decrease rapidly with the $CO_2$ loading. The data shown in FIG. 5 indicate that the energy required for regeneration of adsorbed $CO_2$ in fixed bed adsorbers will be lower for ZJU-35a, ZJU-36a, and MIL-101 than for CuBTC (HKUST-1), MgMOF-74, Cu-TDPAT, NaX, and LTA-5A.

HKUST-1 has the highest, while ZJU-36a has the lowest $CO_2/H_2$ and $CH_4/H_2$ IAST adsorption selectivity among the three isoreticular porous MOFs as shown using IAST calculations taught by Myers and Prausnitz, 1965, which is incorporated herein by reference. The performance of a PSA unit is dictated both by the adsorption selectivity and by the capacity to adsorb both $CO_2$, and $CH_4$. Generally speaking, higher capacities are desirable because the adsorber bed can be run for longer lengths of time before the need for regeneration arises. The sum of the component loadings of $CO_2$ and $CH_4$ in the mixture is an appropriate measure of the capacity. Data on the IAST calculations of the ($CO_2+CH_4$) uptake capacities indicates that ZJU-35a and ZJU-36a have higher uptake capacities than other examined materials for pressures exceeding 2 MPa.

Figure 7A:
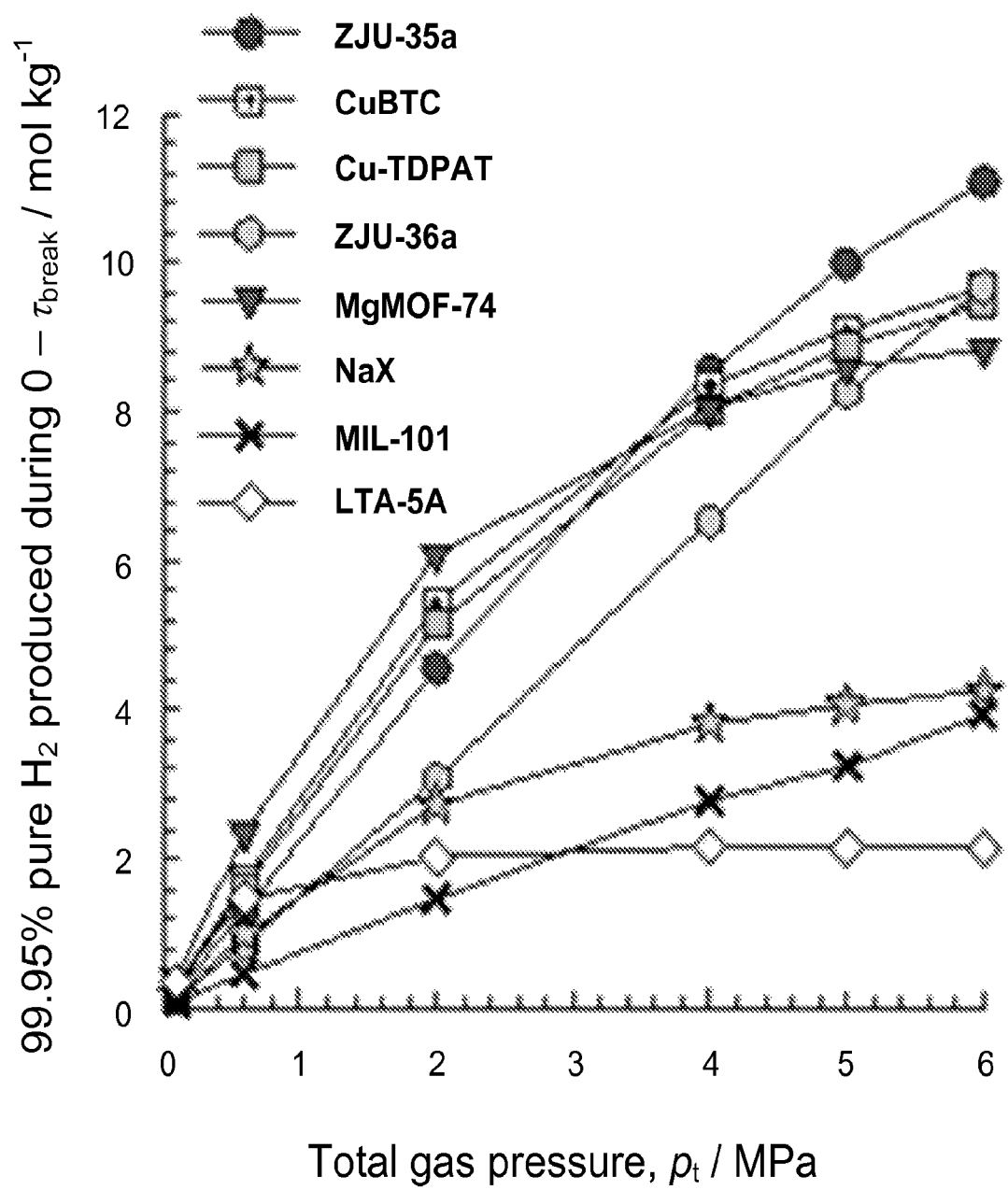
FIGS. 7A-B (A) show the influence of operating pressure on the number of moles of 99.95%+ pure $H_2$ produced per kg of adsorbent material during the time interval $0\text{-}\tau_{break}$. The breakthrough times, $\tau_{break}$, correspond to those when the outlet gas contains 500 ppm ($CO_2+CH_4$) and (B) the influence of operating pressure on the number of moles of 99.95%+ pure $H_2$ produced per L of adsorbent material during the time interval $0\text{-}\tau_{break}$. The breakthrough times, $\tau_{break}$, correspond to those when the outlet gas contains 500 ppm ($CO_2+CH_4$).

Transient breakthrough calculations demonstrate that hydrogen breaks through earliest and it is possible to produce pure hydrogen from this 3-component mixture during the adsorption cycles of both ZJU-35a and ZJU-36a (FIGS. 6A-B) which are taught by Bloch, et al, 2012, Xiang et al, 2012, He et al, 2012, which is incorporated herein by reference. The most important feature is that ZJU-35a exhibits significantly high gravimetric hydrogen productivity, as shown in FIG. 7A. For pressures exceeding 4 MPa, typical of hydrogen purification, the hierarchy of productivities are ZJU-35a>MgMOF-74≈Cu-TDPAT≈HKUST-1≈ZJU-36a>NaX>MIL-101>LTA-5A. The excellent performance of ZJU-35a is due to the suitable combination of separation selectivities and capacities optimized for $H_2$ purification.

Figure 7B:
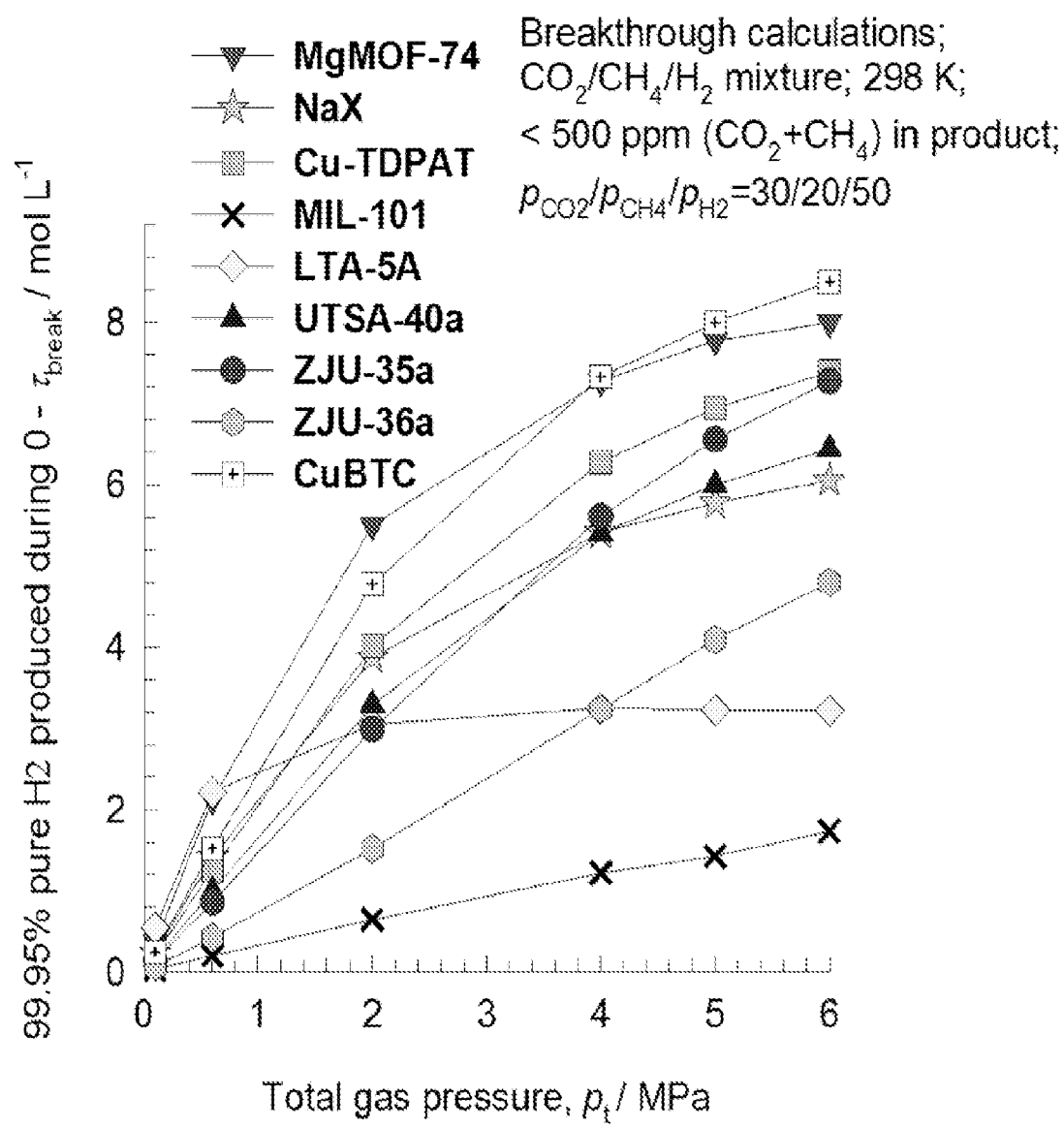

The relative costs of regeneration of the bed will be largely dictated by the desorption of the $CO_2$ captured during the interval $0$-$\tau_{break}$. The energy required for regeneration of adsorbed $CO_2$ in fixed bed adsorbers will be lower for ZJU-35a and ZJU-36a than for HKUST-1, MgMOF-74 and Cu-TDPAT. For pressures exceeding 4 MPa (FIG. 4A-B), ZJU-35a and ZJU-36a have higher gravimetric production capacities than other examined MOFs. Unlike MgMOF-74, both ZJU-35a and ZJU-36a can be easily regenerated without decay. Among the three isoreticular MOFs, ZJU-35a has the highest gravimetric hydrogen production capacity; while HKUST-1 has highest volumetric hydrogen production capacities (FIGS. 7A-B) at high pressures. Overall, ZJU-35a can be ranked as one of the best porous MOFs for high pressure hydrogen purification when regeneration cost, gravimetric and volumetric production capacities need to be balanced considered. The pore and channel sizes/curvatures, pore surface functionalities, pore volumes and framework densities should be equally considered and optimized in order to further realize better MOF materials for high pressure hydrogen purification in the near future.

IV. Examples

The following examples are included to demonstrate particular embodiments of the invention. It should be appreciated by those of skill in the art that the techniques disclosed in the examples which follow represent techniques discovered by the inventor to function well in the practice of the invention, and thus can be considered to constitute particular modes for its practice. However, those of skill in the art should, in light of the present disclosure, appreciate that many changes can be made in the specific embodiments which are disclosed and still obtain a like or similar result without departing from the spirit and scope of the invention.

Materials and Methods.

All of the chemicals were obtained from commercial sources and were used without further purification. IR spectra were collected from KBr pellets on a FTS-40 spectrophotometer. Thermogravimetric analyses (TGA) were carried out under $N_2$ atmosphere on a SDT Q600 instrument at a heating rate of $10°$ C. $min^{-1}$ Elemental analyses were performed on a ThermoFinnigan Flash EA 1112 Element Analyzer. Powder X-ray diffraction (PXRD) data were recorded on a RIGAKU D/MAX 2550/PC for Cu—K$\alpha$ radiation ($\lambda$=1.5406 Å). $^1H$ NMR and $^{13}C$ NMR spectra were recorded on a 500 MHz spectrometer in $CDCl_3$ or $d_6$-DMSO solution and the chemical shifts were reported relative to internal standard TMS (0 ppm).

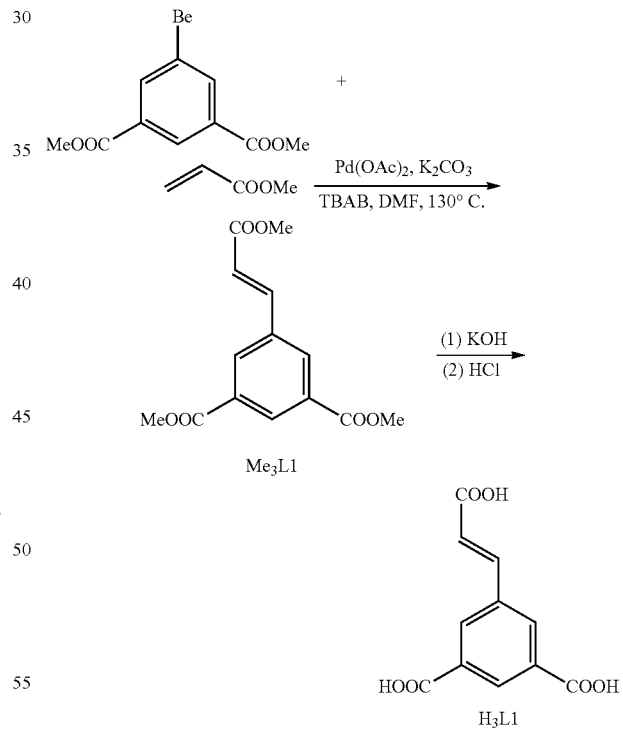

Scheme S1. The synthesis procedure for $H_3L1$.

Synthesis of dimethyl 5-(3-methoxy-3-oxoprop-1-enyl)isophthalate ($Me_3L1$)

Dimethyl 5-bromo-1,3-benzenedicarboxylate (13.65 g, 50 mmol), methyl acrylate (9 mL, 100 mmol), $K_2CO_3$ (10.35 g, 75 mmol), tetrabutyl ammonium bromide (TBAB) (3.22 g, 10 mmol), $Pd(OAc)_2$ (1.122 g, 5 mmol) and DMF (100 mL)

were mixed in a 250 mL round-bottom flask. The mixture was heated at 130° C. under stirring for 24 h. After the reaction was cooled down to room temperature, the mixture was poured into water and extracted with ethyl acetate for three times. The combined organic phase was dried over anhydrous MgSO$_4$ and concentrated in vacuum. The residue was subjected to chromatography on silica gel (petroleum ether/CH$_2$Cl$_2$=5). The solvent was removed under reduced pressure to give white power. Yield: 8.3 g (60%). $^1$H NMR (500 MHz, CDCl$_3$): δ=3.83 (s, 3H), 3.97 (s, 6H), 6.58 (d, J=16.0 Hz, 1H), 7.73 (d, J=16.0 Hz, 1H), 8.36 (s, 2H), 8.67 (s, 1H). $^{13}$C NMR (125 MHz, CDCl$_3$): δ=51.9, 52.6, 120.4, 131.4, 131.8, 132.8, 135.3, 142.5, 165.8, 166.8. IR (KBr pellet, ν/cm$^{-1}$): 1733(s), 1644(m), 1560(w), 1448(m), 1436(m), 1342(m), 1253(s), 1207(m), 1176(s), 1130(w), 994(m), 860(w), 755(m), 596(w).

Synthesis of 5-(2-carboxyvinyl)isophthalic acid (H$_3$L1): Me$_3$L1

(3.9 g, 14 mmol) and KOH (210 mmol, 11.7 g) in 50 mL THF and 50 mL H$_2$O were heated at 60° C. for 12 h. After the mixture was cooled down to room temperature, THF was evaporated under reduced pressure. The pH value of the mixture was adjusted to 1 by concentrated HCl. The precipitate was collected by filtration, washed with water for several times, and dried at 50° C. to afford white powder. Yield: 3.2 g (97%). $^1$H NMR (500 MHz, d$^6$-DMSO): δ=6.64 (d, J=16.0 Hz, 1H), 7.71 (d, J=16.0 Hz, 1H), 8.37 (s, 2H), 8.49 (s, 1H). $^{13}$C NMR (125 MHz, d$^6$-DMSO): δ=121.5, 131.0, 131.9, 133.1, 135.0, 142.0, 166.6, 167.3. IR (KBr pellet, ν/cm$^{-1}$): 1701(s), 1641(m), 1603(w), 1420(m), 1274(s), 1220(s), 1103(w), 982(m), 903(m), 871(w), 763(s), 695(m), 603(m), 519(m).

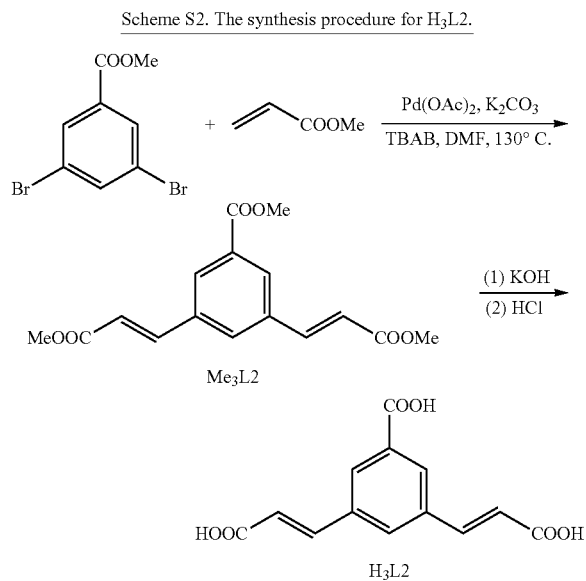

Scheme S2. The synthesis procedure for H$_3$L2.

Synthesis of dimethyl 3,3'-(5-(methoxycarbonyl)-1,3-phenylene)diacrylate (Me$_3$L2)

methyl 3,5-dibromobenzoate (14.7 g, 50 mmol), methyl acrylate (9 mL, 100 mmol), K$_2$CO$_3$ (10.35 g, 75 mmol), tetrabutyl ammonium bromide (TBAB) (3.22 g, 10 mmol), Pd(OAc)$_2$ (1.122 g, 5 mmol) and DMF (100 mL) were mixed in a 250 mL round-bottom flask. The mixture was heated at 130° C. under stirring for 24 h. After the reaction was cooled down to room temperature, the mixture was poured into water and extracted with ethyl acetate for three times. The combined organic phase was dried over anhydrous MgSO$_4$ and concentrated in vacuum. The residue was subjected to chromatography on silica gel (petroleum ether/CH$_2$Cl$_2$=5). The solvent was removed under reduced pressure to give white power. Yield: 9.9 g (65%). $^1$H NMR (500 MHz, CDCl$_3$): δ=3.83 (s, 6H), 3.96 (s, 3H), 6.53 (d, J=16.0 Hz, 2H), 7.70 (d, J=16.0 Hz, 2H), 7.79 (s, 1H), 8.20 (s, 2H). $^{13}$C NMR (125 MHz, CDCl$_3$): δ=51.9, 52.6, 120.1, 130.0, 131.5, 131.7, 135.6, 142.8, 165.9, 166.8. IR (KBr pellet, ν/cm$^{-1}$): 1735(s), 1712(s), 1643(s), 1597(w), 1445(s), 1346(m), 1315(m), 1290(m), 1254(s), 1173(s), 1024(w), 1003(m), 920(w), 860(m), 769(m), 666(w), 562(w).

Synthesis of 3,3'-(5-carboxy-1,3-phenylene)diacrylic acid (H$_3$L2): Me$_3$L2

(3.0 g, 10 mmol) and KOH (210 mmol, 11.7 g) in 50 mL THF and 50 mL H$_2$O were heated at 60° C. for 12 h. After the mixture was cooled down to room temperature, THF was evaporated under reduced pressure. The pH value of the mixture was adjusted to 1 by concentrated HCl. The precipitate was collected by filtration, washed with water for several times, and dried at 50° C. to afford white powder. Yield: 2.5 g (95%). $^1$H NMR (500 MHz, d$^6$-DMSO): δ=6.74 (d, J=16.0 Hz, 2H), 7.65 (d, J=16.0 Hz, 2H), 8.16 (s, 2H), 8.35 (s, 1H). $^{13}$C NMR (125 MHz, d$^6$-DMSO): δ=121.4, 130.2, 130.4, 133.1, 135.3, 142.3, 166.7, 167.4. IR (KBr pellet, ν/cm$^{-1}$): 1724(s), 1703(s), 1637(s), 1557(w), 1442(m), 1408(m), 1293(m), 1254(m), 1216(s), 981(s), 863(m), 773(m), 691(w), 616(w), 581(w).

Synthesis of [Cu$_3$(L1)$_2$(H$_2$O)$_3$].2DMF.5.5H$_2$O (ZJU-35)

H$_3$L1 (20 mg, 0.085 mmol), Cu(NO$_3$)$_2$.3H$_2$O (40 mg, 0.17 mmol), 0.1 M HCl (2.8 mL), 20 mL DMF and 12 mL H$_2$O were mixed and heated at 65° C. for two days. Blue crystals of ZJU-35 were collected by filtration, washed with EtOH and Et$_2$O, and dried in air. Yield: 75%. Anal. Calcd. for C$_{28}$H$_{41}$N$_2$Cu$_3$O$_{22.5}$(%): C, 35.17; H, 4.32; N, 2.93. Found: C, 35.13; H, 4.15; N, 2.87. IR (KBr pellet, ν/cm$^{-1}$): 1652(s), 1614(m), 1560(m), 1497(w), 1440(m), 1378(s), 1262(m), 1107(w), 984(w), 874(w), 777(m), 730(m), 628(w).

Synthesis of [Cu$_3$(L2)$_2$(H$_2$O)$_3$].5DMF.6.5H$_2$O (ZJU-36)

H$_3$L2 (20 mg, 0.076 mmol), Cu(NO$_3$)$_2$.3H$_2$O (40 mg, 0.17 mmol), 0.1 M HCl (5.4 mL), 20 mL DMF and 4 mL H$_2$O were mixed and heated at 65° C. for two days. Blue crystals of ZJU-36 were collected by filtration, washed with EtOH and Et$_2$O, and dried in air. Yield: 79%. Anal. Calcd. for C$_{41}$H$_{68}$N$_5$Cu$_3$O$_{26.5}$(%): C, 39.53; H, 5.50; N, 5.62. Found: C, 39.43; H, 5.59; N, 5.79. IR (KBr pellet, v/cm$^{-1}$): 1652(s), 1588(m), 1497(w), 1437(m), 1397(s), 1282(m), 1165(w), 1101(m), 984(m), 870(m), 789(m), 754(w), 665 (w), 611(w).

Single Crystal X-Ray Data Collections and Structure Determinations.

The determinations of the unit cells and data collections for the crystals of ZJU-35 and ZJU-36 were performed on an Oxford Xcalibur Gemini Ultra diffractometer with an Atlas detector. The data were collected using graphite-monochromatic enhanced ultra Cu radiation ($\lambda$=1.54178 Å) at 293 K. The data sets were corrected by empirical absorption correction using spherical harmonics, implemented in SCALE3 ABSPACK scaling algorithm taught by Oxford Diffraction Ltd., 2010, which is incorporated by reference herein. The structures of the two compounds were solved by direct methods, and refined by full-matrix least-square methods with the SHELX-97 program package taught by Sheldrick, 1997, which is incorporated herein by reference. The solvent molecules in the two compounds are highly disordered, SQUEEZE subroutine of the PLATON software suit was used to remove the scattering from the highly disordered guest molecules which is taught by Spek, 2003, which is incorporated herein by reference. The resulting new files were used to further refine the structures.

The H atoms on C atoms were generated geometrically.

Crystal data for ZJU-35: C$_{22}$H$_{16}$Cu$_3$O$_{15}$, Mw=710.97, Cubic, Fm-3m, a=29.8307(6) Å, V=26545.5(9) Å$^3$, Z=16, T=293 K, $\rho_{calcd}$=0.712 g cm$^{-3}$, $\mu$=1.384 mm$^{-1}$, F(000)=5680, 8749 reflections, 999 independent reflections, R$_{int}$=0.0294, R$_1$[I>2$\sigma$(I)]=0.0783, wR$_2$=0.2318, GOF=1.003. Crystal data for ZJU-36: C$_{26}$H$_{20}$Cu$_3$O$_{15}$, Mw=763.04, Cubic, Fm-3m, a=33.6167(7) Å, V=37989.6 (14) Å$^3$, Z=16, T=293 K, $\rho_{calcd}$=0.534 g cm$^{-3}$, $\mu$=0.982 mm$^{-1}$, F(000)=6128, 7843 reflections, 1367 independent reflections, R$_{int}$=0.0783, R$_1$[I>2$\sigma$(I)]=0.0682, wR$_2$=0.1560, GOF=1.037. CCDC-898168 and 900115 contains the supplementary crystallographic data for ZJU-35 and ZJU-36, respectively.

Adsorbents Compared:

The performance of six different adsorbents were compared for separation of CO$_2$/CH$_4$/H$_2$ mixtures. The structural data are provided in Table 2.

TABLE 2

Structural Data on the Different Adsorbents Evaluated in this Study for Comparison Purposes.

| MOFs | Surface area m$^2$ g$^{-1}$ | Pore volume cm$^3$ g$^{-1}$ | Framework density kg m$^{-3}$ |
|---|---|---|---|
| MgMOF-74 | 1800 | 0.573 | 905 |
| MIL-101 | 2674 | 1.38 | 440 |
| CuBTC | 2097 | 0.848 | 879 |
| Cu-TDPAT | 1938 | 0.93 | 782 |
| NaX zeolite | 950 | 0.280 | 1421 |
| LTA-5A | 450 | 0.250 | 1508 |
| ZJU-35a | 2958 | 1.156 | 657 |
| ZJU-36a | 3243 | 1.599 | 496 |

The Data for MgMOF-74 and NaX are from Herm et al., 2011, and Krishna and Long, 2011, which are incorporated herein by reference. The data for MIL-101 are taken from Chowdhury et al., 2012, which is incorporated herein by reference. The data for Cu-TDPAT are from Wu et al., 2012 and the data for LTA-5A are from Pakseresht et al., 2000, and Sircar and Golden, 2000, all of which are incorporated herein by reference.

Fitting of Pure Component Isotherms

ZJU-35a and ZJU-36a:

The pure component isotherm data for CO$_2$, for three different temperatures 240 K, 270 K, and 300 K were fitted with the dual-site Langmuir-Freundlich model $$q = q_{A,sat}\frac{b_A p^{v_A}}{1 + b_A p^{v_A}} + q_{B,sat}\frac{b_B p^{v_B}}{1 + b_B p^{v_B}} \quad (1)$$

with T-dependent parameters b$_A$, and b$_B$ $$b_A = b_{A0}\exp\left(\frac{E_A}{RT}\right); b_B = b_{B0}\exp\left(\frac{E_B}{RT}\right) \quad (2)$$

The isotherm parameters for CO$_2$ are provided in Tables 3 and 5.

TABLE 3

Dual-site Langmuir-Freundlich Parameters for Adsorption of CO$_2$ and CH$_4$ in ZJU-35a. The Fits for CO$_2$ are Based on High Pressure Isotherm Data Measured at 240K, 270K, and 300K.

| | Site A | | | | Site B | | | |
|---|---|---|---|---|---|---|---|---|
| | $q_{A,sat}$ mol kg$^{-1}$ | $b_{A0}$ Pa$^{-v_i}$ | $E_A$ kJ mol$^{-1}$ | $v_A$ dimensionless | $q_{B,sat}$ mol kg$^{-1}$ | $b_{B0}$ Pa$^{-v_i}$ | $E_B$ kJ mol$^{-1}$ | $v_B$ dimensionless |
| CO$_2$ | 8.6 | 1.10 × 10$^{-13}$ | 27.6 | 1 | 7.4 | 4.12 × 10$^{-10}$ | 23.6 | 1 |
| CH$_4$ | 14 | 1.13 × 10$^{-9}$ | 15 | 1 | | | | |

TABLE 4

1-Site Langmuir Parameters for Pure $H_2$ Isotherms in
ZJU-35a. The Fits are for a Temperature of 298 K.

|  | $q_{A,\,sat}$ mol kg$^{-1}$ | $b_A$ Pa$^{-v_i}$ | $v_A$ dimensionless |
|---|---|---|---|
| $H_2$ | 19 | $3.4 \times 10^{-8}$ | 1 |

TABLE 5

Dual-Site Langmuir-Freundlich Parameters for Adsorption of $CO_2$
and $CH_4$ in ZJU-36a. The Fits for $CO_2$ are Based on High
Pressure Isotherm Data Measured at 240K, 270K, and 300K.

| | Site A | | | | Site B | | | |
|---|---|---|---|---|---|---|---|---|
| | $q_{A,sat}$ mol kg$^{-1}$ | $b_{A0}$ Pa$^{-v_i}$ | $E_A$ kJ mol$^{-1}$ | $v_A$ dimensionless | $q_{B,sat}$ mol kg$^{-1}$ | $b_{B0}$ Pa$^{-v_i}$ | $E_B$ kJ mol$^{-1}$ | $v_B$ dimensionless |
| $CO_2$ | 8.6 | $1.10 \times 10^{-13}$ | 27.6 | 1 | 7.4 | $4.12 \times 10^{-10}$ | 23.6 | 1 |
| $CH_4$ | 14 | $1.13 \times 10^{-9}$ | 15 | 1 | | | | |

TABLE 6

1-Site Langmuir Parameters for Pure $H_2$ Isotherms in
ZJU-36a. The Fits are for a Temperature of 298 K.

|  | $q_{A,\,sat}$ mol kg$^{-1}$ | $b_A$ Pa$^{-v_i}$ | $v_A$ dimensionless |
|---|---|---|---|
| $H_2$ | 19 | $3.4 \times 10^{-8}$ | 1 |

The pure component isotherms of $CH_4$ and $H_2$ do not demonstrate any inflection characteristics and the single-site Langmuir model $$q = \frac{q_{sat} b p}{1 + bp} \quad (3)$$

provides an adequately good representation of the absolute component loadings. The isotherm parameters for $H_2$ are provided in Tables 4 and 6.

Isosteric Heat of Adsorption:

The isosteric heat of adsorption, $Q_{st}$, defined as $$Q_{st} = RT^2 \left( \frac{\partial \ln p}{\partial T} \right)_q \quad (4)$$

were determined using the pure component isotherm fits. The calculations of $-Q_{st}$ are based on the use of the Clausius-Clapeyron equation, using numerical procedures for differentiation of the dual-Langmuir-Freundlich model.

Calculations of Adsorption Selectivity:

The selectivity of preferential adsorption of component 1 over component 2 in a mixture containing 1 and 2, perhaps in the presence of other components too, can be formally defined as $$S_{ads} = \frac{q_1/q_2}{p_1/p_2} \quad (5)$$

In equation (5), $q_1$ and $q_2$ are the absolute component loadings of the adsorbed phase in the mixture. In all the calculations to be presented below, the calculations of $S_{ads}$ are based on the use of the Ideal Adsorbed Solution Theory (IAST) of Myers and Prausnitz, 1965. These calculations are carried out using the pure component isotherm fits of absolute component loadings.

Packed Bed Adsorber Breakthrough Simulation Methodology:

In order to obtain a realistic appraisal of the separation characteristics of various MOFs for $H_2$ purification we perform transient breakthrough calculations. The methodology followed is identical to the ones described in detail in earlier works, as reported in Herm, et al, 2012, Wu, et al., 2012, Krishna, 2011, He, et al., 2012, Krishna and Long, 2011, Krishna and Baur, 2003a, Krishna and Baur, 2003b, Krishna and van Baten, 2012, He et al., 2012a, He, et al., 2012b, He, et al., 2012c, which are incorporated herein by reference. Experimental validation of the breakthrough simulation methodology is also available in the published literature as reported in Wu, et al., 2012, He, et al., 2012, Bloch, et al., 2012, which are incorporated herein by reference.

The following parameter values were used in the simulations to be reported below: L=0.1 m; $\epsilon$=0.4; v=0.1 m/s (at inlet). When comparing different materials, the fractional voidage is held constant at $\epsilon$=0.4. This implies the volumes of adsorbents used in the fixed bed are the same for ZJU-35a, ZJU-36a, CuBTC, MgMOF-74, Cu-TDPAT, MIL-101, NaX, and LTA-5A. The total mass of the adsorbents used is governed by the framework density.

Ternary 30/20/50 $CO_2/CH_4/H_2$ Breakthrough Simulations:

For industrial production of $H_2$, impurities such as $CO_2$ and $CH_4$ need to be reduced to extremely low levels, typically lower than 500 ppm. FIGS. 3A-B show typical concentration profiles at the exit of the adsorber packed with ZJU-35a and ZJU-36a, respectively, and maintained at isothermal conditions at 298 K, and operating at a total pressure of 5 MPa. During the initial period of the fixed bed operation it is possible to recover hydrogen gas of the required purity. From the exit gas concentrations we can determine the ppm ($CO_2+CH_4$) in outlet gas as a function of the dimensionless time dimensionless time, $\tau$, defined by dividing the actual time, t, by the characteristic time, $$\frac{L}{v}.$$

When the composition in the exit gas reaches a certain desired purity level, the adsorption cycle needs to be terminated and the contents of the bed regenerated. Longer breakthrough times are desirable because the longer time reduces the frequency of regeneration. The purity level was chosen to be 500 ppm ($CO_2$+$CH_4$) in outlet gas that is typical of industrial requirements. When this purity level is reached, the corresponding dimensionless breakthrough time, $\tau_{break}$, can be determined.

Additional Ligands:

In some embodiments, the invention provides MOFs based on one or more of the ligands having the formulas listed below, or partially or completely deprotonated forms thereof:

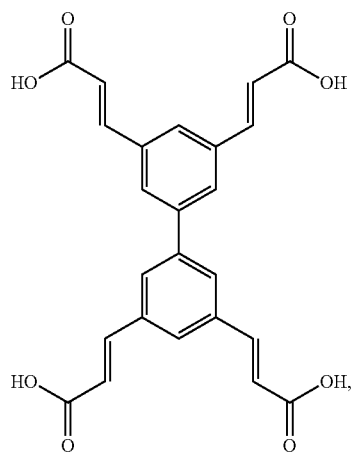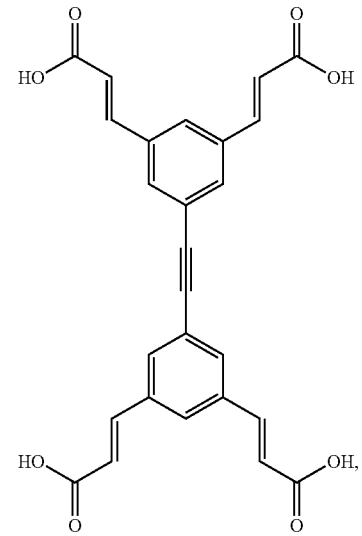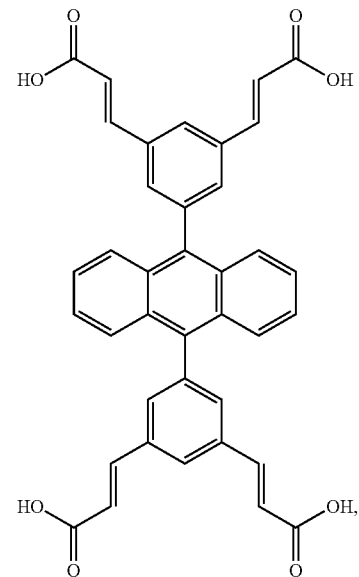

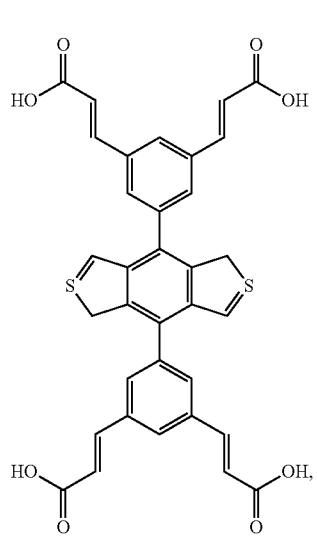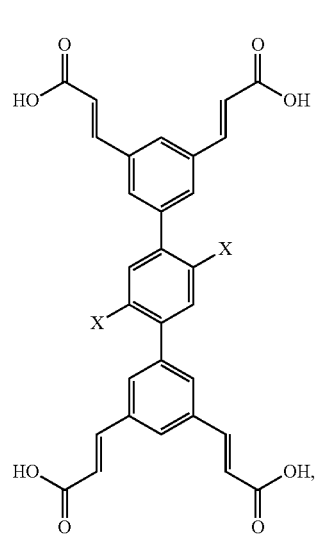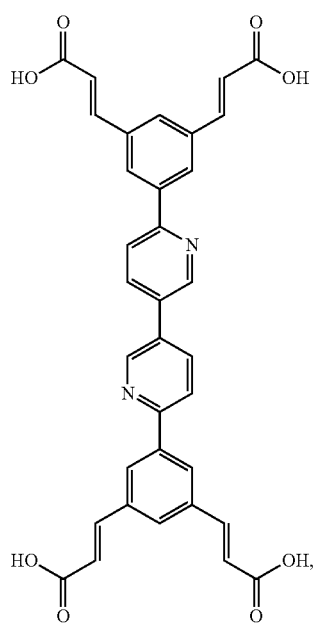

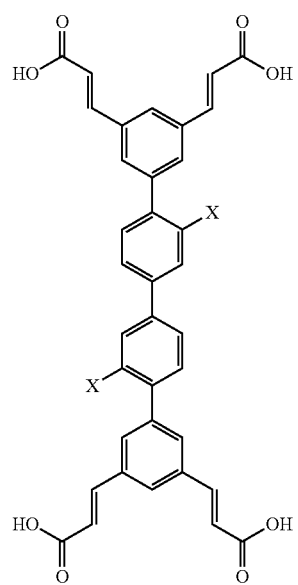
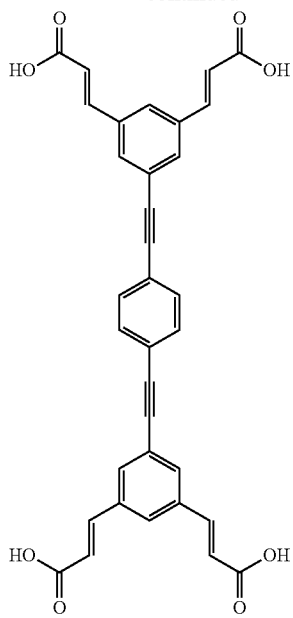
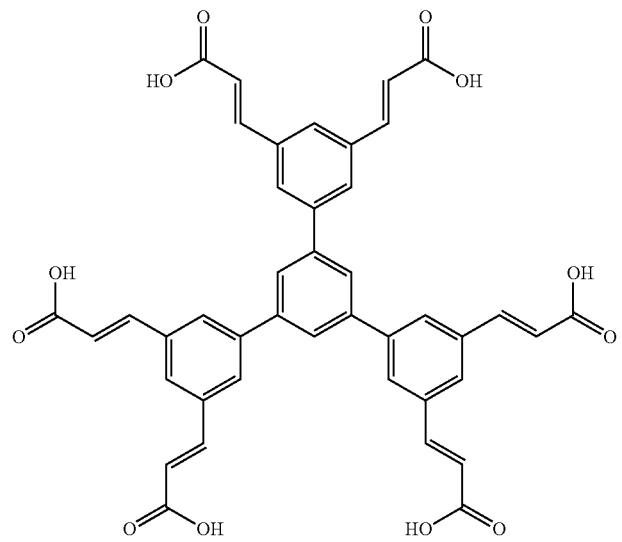

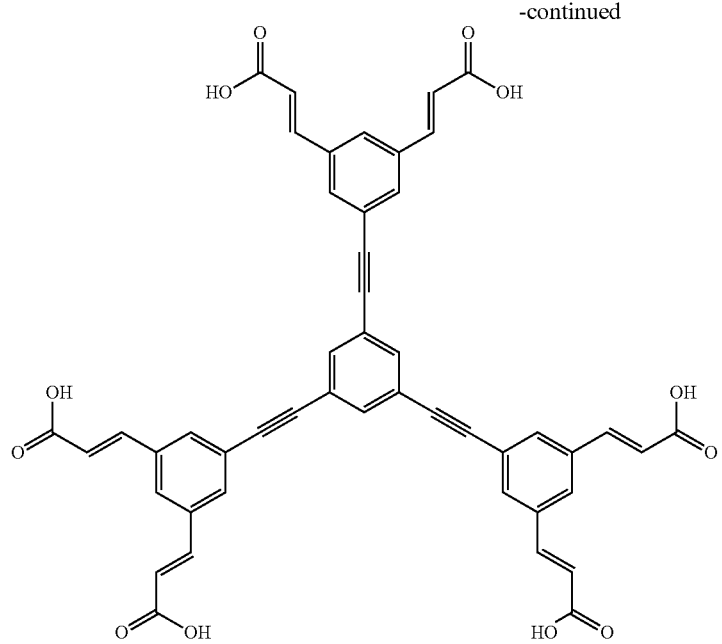
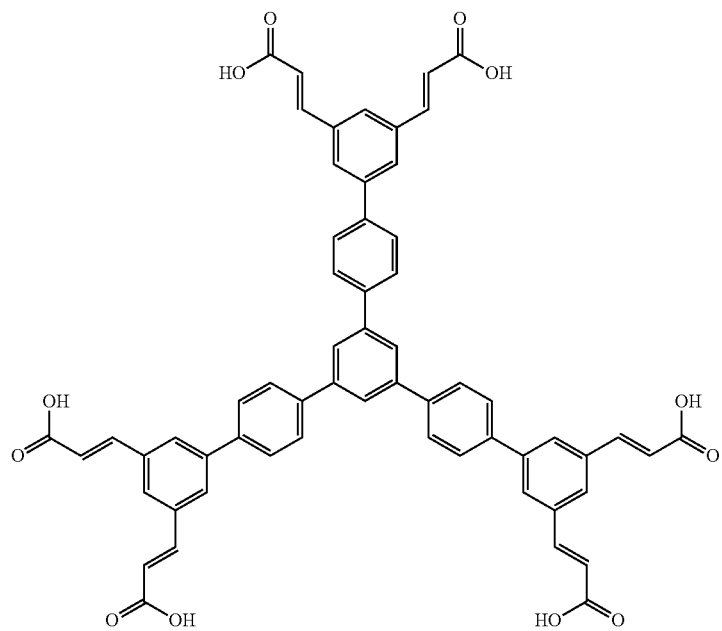

-continued

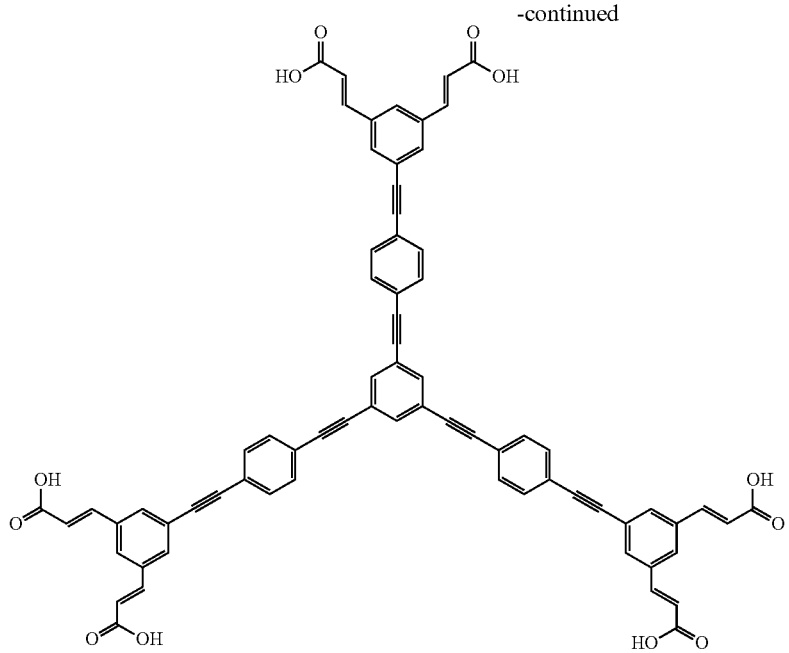

wherein, X is selected independently from —OH, —F, —Cl, —Br, —I, —NH$_2$, —NO$_2$, —CO$_2$H, —CO$_2$CH$_3$, —CO$_2$CH$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, —S(O)$_2$OH or —S(O)$_2$NH$_2$ All of the methods disclosed and claimed herein can be made and executed without undue experimentation in light of the present disclosure. While the compositions and methods of this invention have been described in terms of particular embodiments, it will be apparent to those of skill in the art that variations may be applied to the methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

Bae et al., *Chem. Commun.*, 46:3478, 2010.
Bai et al., *Angew. Chem. Int. Ed.*, 47:5344, 2008.
Bao, et al., *J. Colloid Interface Sci.*, 353:549-556, 2011
Belmabkhout, et al., *Adsorption,* 13:341-349, 2007.
Bloch, et al, *Science* 335:1606-1610, 2012.
Britt et al., *Proc. Natl. Acad. Sci. USA,* 106:20637, 2009.
Cavenati, et al., *J. chem. Eng. Data,* 49:1095-1101, 2004.
Chen et al., *Acc. Chem. Res.*, 43:1115, 2010.
Chen et al., *Angew. Chem. Int. Ed.*, 44:4745-4749, 2005.
Chen et al., *Angew. Chem.*, Int. Ed., 45:1390, 2006.
Chen et al., *Inorg. Chem.*, 43:8209, 2004.
Chen et al., *J. Am. Chem. Soc.*, 130:6411, 2008.
Chen et al., *J. Am. Chem. Soc.*, 131:16027, 2009.
Chen, et al., *Science,* 291:1021, 2001
Cho et al., *Chem. Commun.*, 2563, 2006.
Choudary et al., *Appl. Catal. A,* 181:139, 1999.
Choudary et al., *Microporous Mesoporous Mater.*, 152:246-252, 2012.
Deng et al., *Science,* 327:846, 2010.
Devic et al., *J. Am. Chem. Soc.,* 132:1127, 2010.
Dietzel, et al., *J. Mater. Chem.*, 19:7362-7370, 2009.
Dubbeldam et al., *I. Am. Chem. Soc.,* 130:10884, 2008.
Dybtsev et al., *Angew. Chem.*, Int. Ed., 45:916, 2006.
Dybtsev et al., *J Am. Chem. Soc.,* 126:32, 2004.
Eddaoudi et al., *J. Am. Chem. Soc.,* 122:1391, 2000.
Fang et al., *Angew. Chem.* 118:6272, 2006.
Fang et al., *Chem. Eur. J.,* 12:3754, 2006.
Farha, et al., *Nature Chem.,* 944, 2010.
Farha, et al., *J. Am. Chem. Soc.,* 134:15016, 2012.
Finsy et al., *J. Am. Chem. Soc.,* 130:7110, 2008.
Furukawa, et al., *Inorg. Chem.,* 50:9147, 2011
Furukawa, et al., *Science,* 329:424-428, 2010.
Gedrich, et al., *Angew. Chem. Int. Ed.,* 49:8489-8452, 2010.
Grünker, et al., *Chem. Eur. J.,* 18:13299-13303, 2012
Guo, et al, *Angew. Chem. Int. Ed.,* 50:3178-3181, 2011.
Guo, et al, *J. Am. Chem. Soc.,* 131:1646, 2009.
He, et al, *Chem. Eur. J.,* 18:613-619, 2012
He, et al, *Chem. Commun.,* 48:6493-6495, 2012
He, et al, *Chem Eur. J.,* 18:1901-1904, 2012
He, et al., *J. Mater. Chem. A.,* 2013 DOI:10.1039/C2TA01260J
He, et al, *Energy Environ. Sci.* 5:9107, 2012
Herm, et al., *J. Am. Chem. Soc.,* 133:5664, 2011
Herm, et al., *Micropor. Mesopor. Mater.,* 157:94, 2012
Herm, et al., *Micropor. Mesopor. Mater.,* 151:481-487, 2012
Horike et al., *Nature Chem.,* 1:695, 2009.
Hu, et al., *Chem. Commun.,* 7551, 2009
Kaye, et al., *J. Am. Chem. Soc.,* 129:14176-14177, 2007
Kesanli et al., *Angew. Chem.*, Int. Ed., 44:72, 2005.
Kitaura et al., *Angew. Chem.*, Int. Ed., 43:2684, 2004.
Krishna, R. *Microporous, Mesoporous, Mater.,* 156:249-260, 2012.
Krishna and Long, *J. Phys. Chem. C.,* 115:12941-12950, 2011.
Krishna and Baur, *Sep. Purif. Technol.,* 33:213-254, 2003.

Krishna and Baur, Diffusion, Adsorption and Reaction in Zeolites: Modelling and Numerical Issues, http://www.science.uva.nl/research/cr/zeolite/, University of Amsterdam, Amsterdam, 11 Nov. 2003.
Krishna and van Baten, *Sep. Purif. Technol.* 8:120-126, 2012.
Kuznicki et al., *Nature,* 412:720, 2001.
Latroche, et al., *Angew. Chem. Int. Ed.,* 45:8227-8231, 2006
Lee, et al., *Angew. Chem,* Int. Ed., 47:7741, 2008.
Li et al., *Angew. Chem. Int. Ed.,* 51:1412-1415, 2011.
Li et al., *J. Am. Chem. Soc.,* 131:10368, 2009.
Lin et al., *Angew. Chem.,* Int. Ed., 45:7358, 2006.
Liu et al., *Adv. Mater.,* 22:4112, 2010.
Liu et al., *Chem. Sci.,* 3:3032, 2012.
Llewllyn, et al., *Langmuir,* 24:7245, 2008.
Lu, et al., *Angew. Chem. Int. Ed.,* 51:1580, 2012
Ma and Lin, *Angew. Chem., Int. Ed.,* 48:3637-3640, 2009.
Ma et al., *J. Am. Chem. Soc.,* 129:1858-1859, 2007
Ma et al., *J. Am. Chem. Soc.,* 130:15896-15902, 2008.
Ma et al., *J. Am. Chem. Soc.,* 131:6445, 2009.
Ma et al., *Nature Chem.,* 2:838, 2010.
Mason, et al., *Energy Environ. Sci.,* 3:3030-3040, 2011.
McKinlay et al., *J Am. Chem. Soc.,* 130:10440, 2008.
Moellmer, et al., *Microporous Mesoporous Mater.,* 138:140-148, 2011.
Morris and Bu, *Nature Chem.,* 2:353, 2010.
Murray et al., *J. Am. Chem. Soc.,* 132:7856, 2010.
Myers and Prausnitz, *A.I.Ch.E.J.,* 11:121, 1965
Nuzhdin et al., *J. Am. Chem. Soc.,* 129:12958, 2007.
Oxford Diffraction Ltd., CrysAlisPro, Version 1.171.56, 2010.
Pakseresht, et al., *Sep. Purif. Technol.,* 28: 53-60, 2002.
Peterson, et al, *Angew. Chem. Int. Ed.,* 49:585, 2010.
Rabone et al., *Science,* 329:1053, 2010.
Seo et al., *Nature,* 404:982, 2000.
Sheldrick, G. M., Program for Structure Refinement, University of Göttingen, Germany, 1997.
Shimomura et al., *Nature Chem.,* 2:633, 2010.
Sircar and Golden, *Sep. Sci. and Technol.,* 35:667-687, 2000.
Spek, A. L., *J. Appl. Crystallogr.,* 36:7, 2003.
Spek, In: *PLATON, A Multipurpose Crystallographic Tool,* Utrecht University, Utrecht, The Netherlands, 2001.
Sun, et al., *J. Am. Chem. Soc.,* 128:3896, 2006.
Sun, et al, *J. Am. Chem. Soc.,* 131:1883, 2009.
Vaidhyanathan et al., *Angew. Chem.,* Int. Ed., 45:6495, 2006.
Wang et al., *Angew. Chem.,* Int. Ed., 48:5291-5295, 2009.
Wang, et al., *Inorg. Chem.* 48:7519, 2009
Wu, et al., *J. Phys. Chem. C.,* 116:16609, 2012
Wu, et al, *Angew. Chem. Int. Ed.,* 50:12518, 2011.
Xiang, et al, *Nat. Commun.,* 3:954, 2012
Xiao, et al, *J. Am. Chem. Soc.,* 129:1203, 2007
Xie et al., *J. Am. Chem. Soc.,* 132:922, 2010.
Yaghi, O. M. Hydrogen Storage in Metal Organic Frameworks, www.hydrogen.energy.gov/pdfs/review11/st049_yaghi_2011_p.pdf, University of California Los Angeles, Calif., 2011.
Yan, et al., *J. Am. Chem. Soc.,* 132:4092, 2010.
Yang et al., *Nature Chem.,* 1:487, 2009.
Yuan, et al., *Angew. Chem.,* Int. Ed., 49:5357, 2010.
Zhang et al., *J. Am. Chem. Soc.,* 130:6010, 2008.
Zheng et al., *J. Am. Chem. Soc.,* 133:748, 2011.

The invention claimed is:

1. A metal-organic framework (MOF) comprising a repeat unit of the formula $[Cu_3(L1)_2(H_2O)_3]$ or $[Cu_3(L2)_2(H_2O)_3]$, wherein L1 is a ligand of the formula:

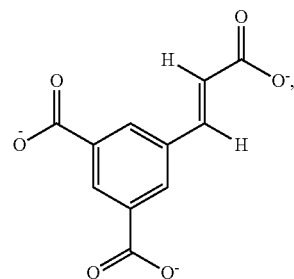

and
wherein L2 is a ligand of the formula:

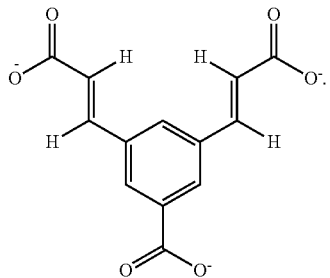

2. The MOF of claim 1, wherein the repeat unit is of the formula $[Cu_3(L1)_2(H_2O)_3]$.
3. The MOF of claim 2, wherein the MOF is activated for sorption of gas molecules.
4. The MOF of claim 1, wherein the repeat unit is of the formula $[Cu_3(L2)_2(H_2O)_3]$.
5. The MOF of claim 4, wherein the MOF is activated for sorption of gas molecules.
6. The MOF of claim 1, further comprising one or more than one type of guest molecule.
7. The MOF of claim 6, wherein one type of guest molecule is a solvent molecule.
8. The MOF of claim 7, wherein the solvent molecule is water.
9. The MOF of claim 7, wherein the solvent molecule is N,N'-dimethylformamide.
10. The MOF of claim 1, further comprising about two N,N'-dimethylformamide and five and half water molecules per repeat unit.
11. The MOF of claim 1, further comprising about five N,N'-dimethylformamide and six and half water molecules per repeat unit.
12. The MOF of claim 7, wherein the solvent molecules occupy the pores of the MOF.
13. The MOF of claim 6, wherein one type of guest molecule is a gas molecule.
14. The MOF of claim 13, wherein the gas molecule is $H_2$, $CO_2$, or $CH_4$.
15. The MOF of claim 14, wherein the gas molecule is $CO_2$.
16. The MOF of claim 14; wherein the gas molecule is $CH_4$.
17. The MOF of claim 14; wherein the gas molecule is $H_2$.
18. The MOF of claim 14, wherein the gas molecule is $CO_2$ and $CH_4$.
19. The MOF of claim 1, wherein the MOF is substantially free from any solvent molecules.
20. The MOF of claim 1, having a weight percentage at least 90% attributable to repeat units of the formula $[Cu_3(L1)_2(H_2O)_3]$ or $[Cu_3(L2)_2(H_2O)_3]$.

21. The MOF of claim 1, having a weight percentage at least 95% attributable to repeat units of the formula [$Cu_3(L1)_2(H_2O)_3$] or [$Cu_3(L2)_2(H_2O)_3$].

22. The MOF of claim 1, having a weight percentage at least 99% attributable to repeat units of the formula [$Cu_3(L1)_2(H_2O)_3$] or [$Cu_3(L2)_2(H_2O)_3$].

23. The MOF of claim 1, wherein the MOF has been adhered to a fixed surface.

24. A method of separating two or more compounds using an MOF comprising:
   (a) obtaining a MOF comprising a repeat unit of the formula [$Cu_3(L1)_2(H_2O)_3$] or [$Cu_3(L2)_2(H_2O)_3$], wherein L1 is a ligand of formula:

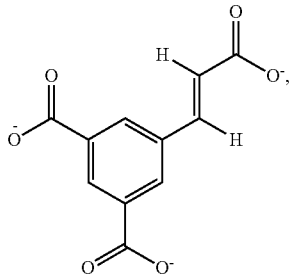

and L2 is a ligand of formula:

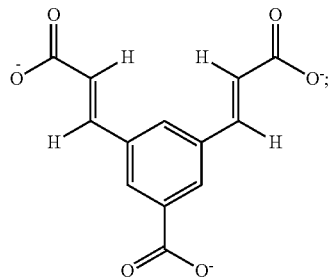

(b) combining the MOF with a mixture comprising a first compound and one or a group of second compounds; and
   (c) separating the two or more compounds based on their differential sorption rate within the MOF.

25. The method of claim 24, wherein the compounds are gas molecules.

26. The method of claim 25, wherein the first compound is $H_2$.

27. The method of claim 25, wherein the second compound is $CH_4$ or $CO_2$.

28. The method of claim 25, wherein the second compound is $CH_4$ and $CO_2$.

29. The method of claim 26, wherein the second compound is $CH_4$ and $CO_2$.

30. The method of claim 24, wherein the separation is carried out at high pressure.

31. The method of claim 30, wherein the separation is carried out at pressures above 2 mPa.

32. The method of claim 31, wherein the separation is carried out at pressures above 4 mPa.

33. The method of claim 24, wherein the MOF is adhered to a fixed surface.

34. The method of claim 24, wherein an absorber is packed with the MOF.

35. The method of claim 24, wherein the absorption is carried out at any temperature.

36. The method of claim 35, wherein the absorption is carried out at room temperature.

37. A method wherein the MOF of claim 1 is used in an application selected from the group consisting of, heterogeneous catalysis, drug delivery, lithium sulfide battery, membrane and analytical devices.

* * * * *